US006451567B1

(12) United States Patent
Barclay

(10) Patent No.: US 6,451,567 B1
(45) Date of Patent: Sep. 17, 2002

(54) FERMENTATION PROCESS FOR PRODUCING LONG CHAIN OMEGA-3 FATTY ACIDS WITH EURYHALINE MICROORGANISMS

(75) Inventor: William R. Barclay, Boulder, CO (US)

(73) Assignee: Omegatech, Inc., Boulder, CO (US)

( * ) Notice: Subject to any disclaimer, the term of this patent is extended or adjusted under 35 U.S.C. 154(b) by 0 days.

(21) Appl. No.: 09/461,709

(22) Filed: Dec. 14, 1999

Related U.S. Application Data

(63) Continuation of application No. 08/968,628, filed on Nov. 12, 1997, now abandoned, which is a continuation of application No. 08/461,137, filed on Jun. 5, 1995, now Pat. No. 5,688,500, which is a continuation of application No. 08/292,490, filed on Aug. 18, 1994, now Pat. No. 5,518,918, which is a continuation of application No. 07/962,522, filed on Oct. 16, 1992, now Pat. No. 5,340,742, which is a continuation-in-part of application No. 07/911,760, filed on Jul. 10, 1992, now Pat. No. 5,340,594, which is a continuation of application No. 07/580,778, filed on Sep. 11, 1990, now Pat. No. 5,130,242, which is a continuation-in-part of application No. 07/439,093, filed on Nov. 17, 1989, now abandoned, which is a continuation-in-part of application No. 07/241,410, filed on Sep. 7, 1988, now abandoned.

(51) Int. Cl.$^7$ .............................. C12N 1/00; C12N 1/12; C12P 1/02; C12P 39/00; C12P 7/64
(52) U.S. Cl. .......................... 435/134; 435/42; 435/135; 435/171; 435/243; 435/257.1; 435/946
(58) Field of Search ............................ 435/243, 257.1, 435/946, 134, 42, 171, 135

(56) References Cited

U.S. PATENT DOCUMENTS

| | | | |
|---|---|---|---|
| 3,296,079 A | 1/1967 | Griffin | 167/93 |
| 3,647,482 A | 3/1972 | Yueh | 99/141 |
| 3,667,969 A | 6/1972 | Kracauer | 99/141 |
| 3,908,026 A | 9/1975 | Neely et al. | 426/538 |
| 3,908,028 A | 9/1975 | Neely et al. | 426/538 |
| 3,924,017 A | 12/1975 | Lee et al. | 426/548 |
| 4,304,794 A | 12/1981 | Dwivedi et al. | 426/548 |
| 4,670,285 A | 6/1987 | Clandinin et al. | 426/602 |
| 4,758,438 A | 7/1988 | Stroz et al. | 426/3 |
| 4,792,418 A | 12/1988 | Rubin et al. | 554/186 |
| 4,871,551 A | 10/1989 | Spencer | 426/2 |
| 5,012,761 A | 5/1991 | Oh | 119/6 |
| 5,130,242 A | 7/1992 | Barclay | 435/134 |
| 5,133,963 A | 7/1992 | Ise | 424/94.61 |
| 5,272,085 A | 12/1993 | Young et al. | 435/254.2 |
| 5,340,594 A | 8/1994 | Barclay | 426/5 |
| 5,340,742 A | 8/1994 | Barclay | 435/256 |
| 5,415,879 A | 5/1995 | Oh | 426/2 |
| 5,492,828 A | 2/1996 | Premuzic et al. | 435/245 |
| 5,518,918 A | 5/1996 | Barclay | 435/257.1 |
| 5,547,699 A | 8/1996 | Iizuka et al. | 426/615 |
| 5,688,500 A | 11/1997 | Barclay | 424/93.1 |

FOREIGN PATENT DOCUMENTS

| | | |
|---|---|---|
| EP | 0 231 904 A2 | 8/1987 |
| FR | 1/557/635 | 2/1969 |
| JP | 58-196068 | 5/1985 |
| JP | 58-213613 | 6/1985 |
| JP | 60-105471 | 10/1985 |
| WO | WO 88/10112 | 12/1988 |
| WO | WO 89/00606 | 1/1989 |
| WO | WO 91/14427 | 10/1991 |
| WO | WO 92/12711 | 8/1992 |

OTHER PUBLICATIONS

Ainsworth, "Introduction and Keys to Higher Taxa.", pp. 1–7, 1973, in *The Fungi. An Advanced Treatise*, vol. 4B, (G.C. Ainsworth et al. eds., Academic Press).
Bahnweg et al., "A New Approach to Taxonomy of the Thraustochytriales and Labyrinthulales", pp. 131–140, 1986, in *The Biology of Marine Fungi*, (S.T. Moss ed., Cambridge University Press).
Bartnicki–Garcia, "The Cell Wall: A Crucial Structure in Fungal Evolution", pp. 389–403, 1988, in *Evolutionary Biology of the Fungi*, (A.D.M. Rayner et al. eds., Cambridge University Press).
Behrens et al., "Eicosapentaenoic Acid from Microalgae", p. 623, col. 2, abstract No. 193025d, 1989, Chemical Abstracts, vol. 111, No. 21, Nov. 20.
Cavalier–Smith, "The Origin of Nuclei and of Eukaryotic Cells", pp. 463–468, 1975, *Nature*, vol. 256.
Cerda–Olmeda et al., "A Biography of *Phycomyces*", pp. 7–26, 1987, in *Phycomyces*, (Cerda–Olmeda et al. eds., CSH Laboratory).
Couch et al., 1973, *Lipids*, 8(7):385–392.
Cruickshank, 1934, "Studies in Fat Metabolism in the Fowl" in *Biochem. J.*, 28:965–977.
Dick, "Saprolegniales", pp. 113–144, 1973, in *The Fungi. An Advanced Treatise*, (G.C. Ainsworth et al. eds., Academic Press).

(List continued on next page.)

Primary Examiner—David M. Naff
Assistant Examiner—Deborah K. Ware
(74) Attorney, Agent, or Firm—Sheridan Ross P.C.

(57) ABSTRACT

A process is provided for growing the microflora Thraustochytrium, Schizochytrium, and mixtures thereof, which includes the growing of the microflora in fermentation medium containing non-chloride containing sodium salts, in particular sodium sulfate. In a preferred embodiment of the present invention, the process produces microflora having a cell aggregate size useful for the production of food products for use in aquaculture. Further disclosed is a food product which includes Thraustochytrium, Schizochytrium, and mixtures thereof, and a component selected from flaxseed, rapeseed, soybean and avocado meal. Such a food product includes a balance of long chain and short chain omega-3 highly unsaturated fatty acids. Further, a process for producing lipids includes a fermentation by growing euryhaline microorganisms which are capable of producing 1.08 grams per liter of the fermentation medium per day of long chain omega-3 fatty acids per 40 grams of sugar per liter of the fermentation medium at a sodium ion concentration of 60% seawater. The lipids are then extracted from the euryhaline microorganisms.

14 Claims, 8 Drawing Sheets

OTHER PUBLICATIONS

Ellenbogen, "Polyunsaturated Fatty Acids of Aquatic Fungi: Possible Phylogenetic Significance", pp. 805–811, 1969, *Comp. Biochem. Physiol.*, vol. 29.

Emerson, "Current Trends of Experimental Research in the Aquatic Phycomycetes", pp. 169–200, 1950, *Ann. Rev. Micro.*, vol. 4.

Erwin, "Comparative Biochemistry of Fatty Acids in Eukaryotic Micoorganisms", pp. 41–143, 1973, in *Lipids and Biomembranes of Eukaryotic Microorganisms*, (J. Erwin ed., Academic Press.

Findlay et al., "Biochemical Indicators of the Role of Fungi and Thraustrochytrids in Mangrove Detrital Systems", pp. 91–103, 1986, in *The Biology of Marine Fungi*, (S.T. Moss ed., Cambridge University Press).

Fisher et al., 1957, *J. Nutr.*, 63:119–129.

Fuller, et al., "Isolation and Pure Culture Study of Marine Phycomycetes", pp. 745–756, 1964, *Mycologia*, vol. 56.

Gellerman et al., "Methyl–Directed Desaturation of Arachidonic to Eicosapentaenoic Acid in the Fungus, *Saprolegnia Parasitica*", pp. 23–30, 1979, *Biochim. Biophys. Acta*, vol. 573.

Goldstein, "Development and Nutrition of New Species of Thraustochystrium", pp. 271–279, 1963, *Am. J. Bot.*, vol. 50.

Goldstein et al., "Biology of a Problematic Marine Fungus, Dermocystidium sp. II. Nutrition and Respiration", pp. 468–472, 1969, *Mycologia*, vol. 61.

Goldstein et al., "Biology of a Problematic Marine Fungus, Dermocystidium sp. I. Development and Cytology", pp. 1–11, 1966, *Archiv for Mikrobiologie*, vol. 53.1.

Henderson et al., "Lipid Composition and Biosynthesis in the Marine Dinoflagellate Crypthecodinium Cohnii", pp. 1679–1683, 1988, *Phytochemistry*, vol. 27. No. 6.

Hori et al., "The Nucleotide Sequence of 5S rRNA from a Cellulai Slime Mold *Dictyostelium Discoideum*", pp. 5535–5539, 1980, *Nucl. Acids Res.*, vol. 8.

Hunter, "Fish Oil and Other Omega–3 Sources", pp. 1592–1596, 1987, *J. Am. Oil Chem. Soc.*, vol. 64.

Jong et al., "American Type Culture Collection Catalogue of Fungi/Yeast", pp. 350 and 378, *American Type Culture Collection*, 17th Edition, 1987.

Kates, "Techniques of Lipidology: Isolation, Analysis and Identification of Lipids", pp. 186–278, 1986, *Laboratory Techniques in Biochemistry and Molecular Biology*, vol. 3.

Kyle, "Microalgae as a Source of EPA–Containing Oils", p. 1251, 1987, *J. Am. Oil Chem. Soc.*, vol. 64.

Lepage et al., "Improved Recovery of Fatty Acid Through Direct Transesterification Without Prior Extraction or Purification", pp. 1391–1396, 1984, *J. Lipid Res.*, vol. 25.

Lipstein et al., "The Nutritional and Economic Value of Algae for Poultry" in *Algae Biomass*, G. Shelef and C.J. Soeder, eds., Elsevier/North–Holland Biomedical Press, 1980, pp.667–685.

Lipstein et al., 1980, *Br. Poultry Sci.*, 21:9–21.

Mannella et al., "Interrelatedness of 5S RNA Sequences Investigated by Correspondence Analysis", pp. 228–235, 1987, *J. Mol. Evol.*, vol. 24.

Miller, "Isolation and Pure Culture of Aquatic Phycomycetes by Membrane Filtration", pp. 524–527, 1967, *Mycologia*, vol. 59.

Moss, "Biology and Phylogeny of the Labrinthulales and Thraustochytriales", pp. 105–129, 1986, in *The Biology of Marine Fungi*, (S.T. Moss ed., Cambridge University Press).

Murty et al., 1961, *J. Nutrition*, 75:287–294.

Navarro et al., 1972, *J. Sci. Fd. Agric.*, 23:1287–1292.

Perkins, "Phylogenic Considerations of the Problematic Thraustochytriaceous–Labrinthulid–Dermocystidium Complex Based on Observations of Fine Structure", pp. 45–63, 1974, *Veroff. Inst. Meeresforsch. Bremerh. Suppl.*, vol. 5.

Pigot, "The Need to Improve Omega–3 Content of Cultured Fish", pp. 63–68, 1989, *World Aquaculture*, vol. 20.

Pohl et al., "Fatty Acids and Lipids of Marine Algae and the Control of Their Biosynthesis by Environmental Factors", pp. 473–523, 1979, *Marine Algae in Pharmaceutical Science*, (Hoppe et al. eds.).

Reiser, 1951, *J. Nutrition*, 44:159–175.

Ryther, "Cultivation of Macroscopic Marine Algae", pp. 79–88, 1983, *Solar Energy Research Institute Aquatic Species Program Review*. Proc of the Mar. 1983 Principal Investigators Meeting, SERI/CP/–231 1946.

Schlenk, "Urea Inclusion Compounds of Fatty Acids", pp. 243–267, 1954, *Prog. Chem. Fats and Other Lipids*, vol. 2.

Schneider, "Cultivation of Micro–organisms. Section 3.2: Fungi", pp. 337–345, 1976, in *Marine Ecology*, vol. 3, Part 1. Cultivation, (O. Kinne ed., Wiley and Sons).

Simopoulos et al. (eds.), *Health Effects of Polyunsaturated Fatty Acids in Seafoods*, Chaps. 2–5, 7, 17, 1986, Academic Press).

Sorokin, "Dry Weight, Packed Cell Volume and Optical Density", pp. 321–343, 1973 in *Handbook of Psychological Methods: Culture Methods and Growth Measurements*, (J.R. Stein ed., Cambridge University Press).

Sparrow, *Aquatic Phycomycetes*, pp. 36–39, 1960, University of Michigan Press.

Wassef, "Fungal Lipids", pp. 159–232, 1977, *Adv. Lipid Res.*, vol. 15.

Weete, "Fatty Acids", pp. 49–95, 1980, in *Lipid Biochemistry of Fungi and Other Organisms*, (Plenum Press).

Yamada et al., "Production of Arachidonic Acid and Eicosapentaenoic Acid by Microorganisms", p. 1254, 1987, *J. Am. Oil Chem. Soc.*, vol. 64.

Akimoto et al., "Metal Salts Requisite for the Production of Eicosapentaenoic Acid by a Marine Bacterium Isolated from Mackerel Intestines", pp. 504–508, 1991, *JAOCS*, vol. 68, Jul.

Ando et al., "Incorporation of n–3 Polyunsaturated Fatty Acids into Phospholipids of a Marine Bacterium *Vibrio* sp. Cultivated with Sardine Oil", pp. 169–171, 1992, *J. Ferm. Bioeng.*, vol. 73.

Bajpai et al., "Production of Docosahexaenoic Acid by *Thraustochytrium aureum*", pp. 706–710, 1991, *Appl. Microbiol. Biotechnol.*, vol. 35.

Bajpai et al., "Effects of Aging *Mortierella* Mycelium on Production of Arachidonic and Eicosapentaenoic Acids", pp. 775–780, 1991, *JAOCS*, vol. 68, Oct.

Bajpai et al., Optimization of Production of Docosahexaenoic Acid (DHA) by *Thraustochytrium aureum* ATCC 34304, pp. 509–514, 1991, *JAOCS*, vol. 68, Jul.

Bajpai et al., "Eicosapentaenoic Acid (EPA) Formation; Comparative Studies with *Mortierella* Strains and Production by *Mortierella elongata*", pp. 1294–1298, 1991, *Mycol. Res.*, vol. 95.

Behrens et al., "Eicosapentaenoic Acid from Microalgae", pp. 253–259, 1989, *Novel Microb. Prod. Med. Agric.*

Boswell et al., "SCO Production by Fermentative Microalgae", pp. 274–286, 1992 in *Industrial Applications of Single Cell Oils* (Kyle et al., eds.), American Oil Chemists' Society, Champaign, IL.

Cohen et al., "Overproduction of γ–linolenic and Eicosapentaenoic Acids by Algae", pp. 569–572, 1992, *Plant Physiol.*, vol. 98.

Gandhi et al., Production of the Polyunsaturated Fatty Acids Arachidonic Acids and Elcosapentaenoic Acid by the Fungus *Pythium ultimum*, pp. 1825–1830; 1991, *J. Gen. Microbiol.*, vol. 137.

Hansen et al., Effects of Culture Conditions on Accumulation of Arachidonic and Eicosapentaenoic Acids in Cultured Cells of *Rhytidiadelphus squarrosus* and *Eurhynchium striatum*, pp. 1837–1841, 1991, *Phytochemistry*, vol. 30.

Kendrick et al., "Microbial Polyunsaturated Fatty Acids of Potential Commercial Interest", pp. 59–65, 1992, *SIM Industrial Microbiology NEWS*, vol. 42.

Kendrick et al., "Lipids of Selected Molds Grown for Production of n–3 and n–6 Polyunsaturated Fatty Acids", pp. 15–20, 1992, *LIPIDS*, vol. 27.

Kyle et al., "Biproduction of Docosahexaenoic Acid (DHA) by Microalgae", pp. 287–300, 1992, in *Industrial Applications of Single Cell Oils* (Kyle et al., eds.), American Oil Chemists' Society, Champaign, Il.

Kyle et al., "Microalgae as a Source of EPA–Containing Oils", pp. 117–121, 1988, *Proc.—World Conf. Biotechnol. Fats Oils Ind.*

Radwan, "Sources of $C_{20}$–Polyunsaturated Fatty Acids for Biotechnical Use", pp. 421–430, 1991, *Appl. Microbiol. Biotechnol.*, vol. 35.

Yazawa et al., "Production of Eicosapentaenoic Acid from Marine Bacteria", pp. 29–51, 1992, in *Industrial Applications of Single Cell Oils* (Kyle et al., eds.), American Oil Chemists' Champaign, IL.

Yongmanitchai et al., "Screening of Algae for Potential Alternative Sources of Eicosapentaenoic Acid", pp. 2963–2967, 1991, *Phytochemistry*, vol. 30.

Hagemeister et al., STN Database, AN 88:13,222 Biobusiness for Milchwissenschaft, vol. 43, No. 3, pp. 153, 155–158.

T. Long, STN Database, AN 89:532,569 Caplus for WO 88–US2483.

Todorov, D., "Possibilities for increasing the Biological Value of Alimentary Protein", KHIGZDRAVFODAZ, 1978, 21(3), p. 291–297.

Yamada et al., "Production of Dihomo–β–Linolenic Acid, Arachidonic Acid and Eicosapentaenoic Acid by Filamentous Fungi", pp. 118–138, 1992, in *Industrial Applications of Single Cell Oils* (Kyle et al., eds.), American Oil Chemists' Society, Champaign, Il.

Kyle et al., "Microalgae as a Source of EPA–Containing Oils", pp. 117–121, 1988, *Proc. World Conf. Biotechnol. Fats Oils Ind.*

FERMENTATION PROCESS FOR PRODUCING LONG CHAIN OMEGA-3 FATTY ACIDS WITH EURYHALINE MICROORGANISMS

CROSS-REFERENCE TO RELATED APPLICATIONS

This application is continuation-in-part of U.S. patent application Ser. No. 08/968,628, filed Nov. 12, 1997, now abandoned, which is a continuation of U.S. patent application Ser. No. 08/461,137, filed Jun. 5, 1995, which issued as U.S. Pat. No. 5,688,500, which is a continuation of U.S. patent application Ser. No. 08/292,490, filed Aug. 18, 1994, which issued as U.S. Pat. No. 5,518,918, which is a divisional of U.S. patent application Ser. No. 07/962,522, filed Oct. 16, 1992, which issued as U.S. Pat. No. 5,340,742, which is a continuation-in-part of U.S. patent application Ser. No. 07/911,760, filed Jul. 10, 1992, which issued as U.S. Pat. No. 5,340,594, which is a divisional of U.S. patent application Ser. No. 07/580,778, filed Sep. 11, 1990, which issued as U.S. Pat. No. 5,130,242, which is a continuation-in-part of U.S. patent application Ser. No. 07/439,093, filed Nov. 17, 1989, now abandoned, which is a continuation-in-part of U.S. patent application Ser. No. 07/241,410, filed Sep. 7, 1988, now abandoned.

This application is also a continuation-in-part of U.S. patent application Ser. No. 08/918,325, filed Aug. 26, 1997, now U.S. Pat. No. 5,985,348, which is a divisional of U.S. patent application Ser. No. 08/483,477, filed Jun. 7, 1995, now U.S. Pat. No. 5,698,244, which is a continuation-in-part of U.S. patent application Ser. No. 08/292,736, filed Aug. 18, 1994, now U.S. Pat. No. 5,656,319, which is a divisional of U.S. patent application Ser. No. 07/911,760, filed Jul. 10, 1992, now U.S. Pat. No. 5,340,594, which is a divisional of U.S. patent application Ser. No. 07/580,778, filed Sep. 11, 1990, now U.S. Pat. No. 5,130,242, which is a continuation-in-part application of U.S. patent application Ser. No. 07/439,093, filed Nov. 17, 1989, now abandoned, which is a continuation-in-part of U.S. patent application Ser. No. 07/241,410, filed Sep. 7, 1988, now abandoned.

All of the above patents and patent applications are incorporated herein by reference in their entirety.

FIELD OF THE INVENTION

The field of this invention relates to heterotrophic organisms and a process for culturing them for the production of lipids with high concentrations of omega-3 highly unsaturated fatty acids (HUFA) suitable for human and animal consumption as food additives or for use in pharmaceutical and industrial products.

BACKGROUND OF THE INVENTION

Omega-3 highly unsaturated fatty acids (HUFAs) are of significant commercial interest in that they have been recently recognized as important dietary compounds for preventing arteriosclerosis and coronary heart disease, for alleviating inflammatory conditions and for retarding the growth of tumor cells. These beneficial effects are a result both of omega-3 HUFAs causing competitive inhibition of compounds produced from omega-6 fatty acids, and from beneficial compounds produced directly from the omega-3 HUFAs themselves (Simopoulos et al., 1986). Omega-6 fatty acids are the predominant HUFAs found in plants and animals. Currently, a commercially available dietary source of omega-3 HUFAs is from certain fish oils which can contain up to 20–30% of these fatty acids. The beneficial effects of these fatty acids can be obtained by eating fish several times a week or by daily intake of concentrated fish oil. Consequently large quantities of fish oil are processed and encapsulated each year for sale as a dietary supplement. However, there are several significant problems with these fish oil supplements, including bioaccumulation of fat-soluble vitamins and high levels of saturated and omega-6 fatty acids, both of which can have deleterious health effects.

Another source of omega-3 HUFAS is the microflora Thraustochytrium and Schizochytrium which are discussed in detail in related U.S. Pat. No. 5,130,242. These microflora have the advantages of being heterotrophic and capable of high levels of omega-3 HUFA production. There still exists a need however for improved methods for fermentation of these microflora and identification of improved uses of the microflora product.

BRIEF SUMMARY OF THE INVENTION

The present invention is directed to a new process for growing the microflora Thraustochytrium, Schizochytrium, and mixtures thereof, which includes the growing of the microflora in a culture medium containing non-chloride containing sodium salts, particularly including sodium sulfate. More particularly, a significant portion of the sodium requirements of the fermentation are supplied as a non-chloride containing sodium salt. The present process is particularly useful in commercial production because the chloride content in the medium can be significantly reduced, thereby avoiding the corrosive effects of chloride on fermentation equipment. In addition, the present invention is particularly useful for production of food products for use in aquaculture because Thraustochytrium and Schizochytrium cultured in such media form much smaller clumps than those cultured in high chloride media and are thus more available as a food source for larval shrimp. In particular, Thraustochytrium and Schizochytrium cultured in medium containing sodium sulfate can have cell aggregates of an average size of less than about 150 microns in diameter.

A further embodiment of the present invention is the production of a microflora biomass comprising Thraustochytrium, Schizochytrium, and mixtures thereof which have an average cell aggregate size of less than about 150 microns. The microflora biomass is useful for aquaculture and in particular, for feeding larval shrimp because the microflora have the primary feed advantages required for shrimp of a high sterol content and a high omega-3 highly unsaturated fatty acid (HUFA) content. Additionally, because of the small cell aggregate size, the microflora can be eaten by the larval shrimp, brine shrimp, rotifers, and mollusks. The present invention further includes a process for the production of these organisms which includes feeding Thraustochytrium, Schizochytrium, and mixtures thereof, having an average cell size of less than about 150 microns to them.

A further embodiment of the present invention is directed to a food product which is comprised of microflora selected from the group consisting of Thraustochytrium, Schizochytrium, and mixtures thereof and an additional component selected from the group consisting of flaxseed, rapeseed, soybean, avocado meal, and mixtures thereof. A particular advantage of this food product is that it has a high long chain omega-3 fatty acid content and a high short chain omega-3 fatty chain content from the additional component. In a further embodiment, the food product is produced by extrusion. The extrusion process involves mixing the microflora with the additional component, thereby reducing the moisture content of the food product. The food product is then extruded under heat, thus driving off a significant portion of the reduced moisture. The remaining amount of the original moisture content is readily removed by air drying or short baking times, thereby reducing the overall energy requirements of drying and the potential degradation of the omega-3 HUFA's by extended drying at high temperatures.

DETAILED DESCRIPTION OF THE PREFERRED EMBODIMENTS

Figure 1:
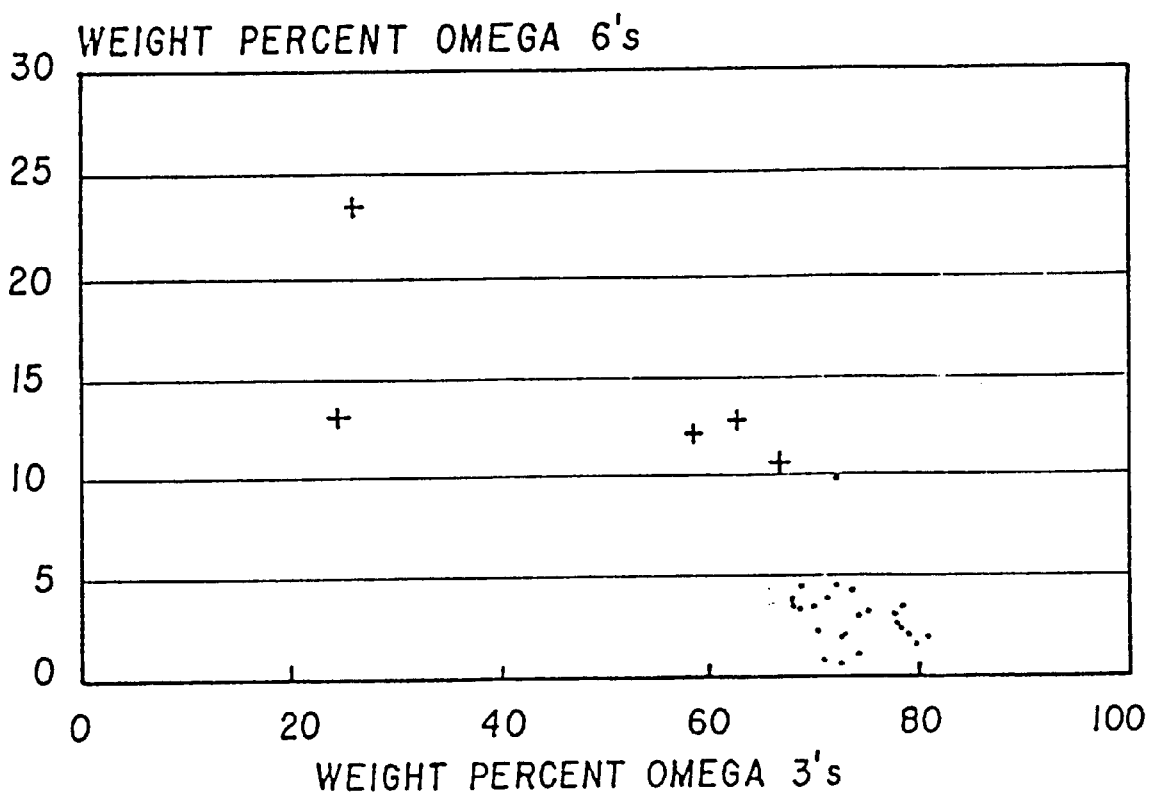
FIG. 1 is a graphical representation of HUFA production in newly isolated strains of the invention, represented by ■, and previously isolated strains represented by +. Each point represents a strain, the position of each point is determined by the percent by weight of total fatty acids which were omega-3 HUFAs (abscissa) and the percent by weight of total fatty acids which were omega-6 fatty acids (ordinate). Only those strains of the invention were plotted wherein less than 10.6% (w/w) of total fatty acids were omega-6 and more than 67% of total fatty acids were omega-3.

For purposes of definition throughout the application, it is understood herein that a fatty acid is an aliphatic monocarboxylic acid. Lipids are understood to be fats or oils including the glyceride esters of fatty acids along with associated phosphatides, sterols, alcohols, hydrocarbons, ketones, and related compounds.

A commonly employed shorthand system is used in this specification to denote the structure of the fatty acids (e.g., Weete, 1980). This system uses the letter "C" accompanied by a number denoting the number of carbons in the hydrocarbon chain, followed by a colon and a number indicating the number of double bonds, i.e., C20:5, eicosapentaenoic acid. Fatty acids are numbered starting at the carboxy carbon. Position of the double bonds is indicated by adding the Greek letter delta ($\Delta$) followed by the carbon number of the double bond; i.e., C20:5omega-3$\Delta^{5,8,11,14,17}$. The "omega" notation is a shorthand system for unsaturated fatty acids whereby numbering from the carboxy-terminal carbon is used. For convenience, n-3 will be used to symbolize "omega-3," especially when using the numerical shorthand nomenclature described herein. Omega-3 highly unsaturated fatty acids are understood to be polyethylenic fatty acids in which the ultimate ethylenic bond is 3 carbons from and including the terminal methyl group of the fatty acid. Thus, the complete nomenclature for eicosapentaenoic acid, an omega-3 highly unsaturated fatty acid, would be C20:5n-3$\Delta^{5,8,11,14,17}$. For the sake of brevity, the double bond locations ($\Delta^{5,8,11,14,17}$) will be omitted. Eicosapentaenoic acid is then designated C20:5n-3, Docosapentaenoic acid (C22:5n-3$\Delta^{7,10,13,16,19}$) is C22:5n-3, and Docosahexaenoic acid (C22:6n-3$\Delta^{4,7,10,13,16,19}$) is C22:6n-3. The nomenclature "highly unsaturated fatty acid" means a fatty acid with 4 or more double bonds. "Saturated fatty acid" means a fatty acid with 1 to 3 double bonds.

A collection and screening process has been developed to readily isolate many strains of microorganisms with the following combination of economically desirable characteristics for the production of omega-3 HUFAs: 1) capable of heterotrophic growth; 2) high content of omega-3 HUFAs; 3) unicellular; 4) preferably low content of saturated and omega-6 HUFAS; 5) preferably nonpigmented, white or essentially colorless cells; 6) preferably thermotolerant (ability to grow at temperatures above 30° C.); and 7) preferably euryhaline (able to grow over a wide range of salinities, but especially at low salinities). This process is described in detail in related U.S. Pat. No. 5,130,242.

Collection, isolation and selection of large numbers of suitable heterotrophic strains can be accomplished by the following method. Suitable water samples and organisms typically can be collected from shallow, saline habitats which preferably undergo a wide range of temperature and salinity variation. These habitats include marine tide pools, estuaries and inland saline ponds, springs, playas and lakes. Specific examples of these collection sites are: 1) saline warm springs such as those located along the Colorado river in Glenwood Springs, Colo., or along the western edge of the Stansbury Mountains, Utah; 2) playas such as Goshen playa located near Goshen, Utah; 3) marine tide pools such as those located in the Bird Rocks area of La Jolla, Calif.;

and 4) estuaries, such as Tiajuana estuary, San Diego County, Calif. Special effort should be made to include some of the living plant matter and naturally occurring detritus (decaying plant and animal matter) along with the water sample. The sample can then be refrigerated until return to the laboratory. Sampling error is minimized if the water sample is shaken for 15–30 seconds, prior to pipetting or pouring a portion, for example, 1–10 ml, into a filter unit. The filter unit includes 2 types of filters: 1) on top, a sterile Whatman #4 filter (Trademark, Whatman Inc., Clifton, N.J.); and 2) underneath the Whatman filter, a polycarbonate filter with 1.0 $\mu$m pore size. The purpose of the first (top) filter is to remove all particulate matter greater than about 25 $\mu$m, generally allowing only unicellular type material to pass onto the 1.0 $\mu$m polycarbonate filter. The first filter greatly reduces the number of mold colonies that subsequently develop upon incubation of the polycarbonate filter at elevated temperatures, thereby enhancing the opportunities for other colonies to develop. Mold spores are very numerous in coastal and inland saline waters, and mold colonies can quickly cover an agar plate unless screened out. The 1.0 $\mu$m size of the polycarbonate filter is chosen to allow many of the bacteria to pass on through into the filtrate. The purpose of using a sandwich filter design is to select for unicellular organisms at least a portion of whose cells range in diameter from about 1 $\mu$m to about 25 $\mu$m in size (organisms which could potentially be grown easily in a fermentor system for production on a large scale). Extensive growth of these unicellular organisms can be encouraged by incubation of the polycarbonate filter on an agar plate. Competition between organisms growing on the filter facilitates the isolation of competitive, robust strains of single-celled microorganisms. Unicellular aquatic microorganisms selected by the foregoing method display a range of cell size depending on growth conditions and stage of reproductive cycle. Most cells in culture have diameters in the range from about 1 $\mu$m to about 25 $\mu$m; however, cells (thalli and sporangia) in the cultures can be found that have larger diameters (depending on the strain) up to about 60 $\mu$m.

After filtration, the polycarbonate filter can be placed on an agar plate containing saline media containing a source of organic carbon such as carbohydrate including glucose, various starches, molasses, ground corn and the like, a source of assimilable organic or inorganic nitrogen such as nitrate, urea, ammonium salts, amino acids, microbial growth factors included in one or more of yeast extract, vitamins, and corn steep liquor, a source of assimilable organic or inorganic phosphorous, and a pH buffer such as bicarbonate. Microbial growth factors are currently unspecified compounds which enhance heterotrophic growth of unicellular microorganisms, including fungi and algae. The agar plates can be incubated in the dark at 25°–35° C. (30° C. is preferred) and after 2–4 days numerous colonies will have appeared on the filter. Recovery of 1–5 colonies/plate of the desired organism is not uncommon. Yeast colonies are distinguishable either by color (they frequently are pink) or by their morphology. Yeast colonies are smooth whereas the desired organisms form in colonies with rough or textured surfaces. Individual cells of the desired organism can be seen through a dissecting microscope at the colony borders, whereas yeast cells are not distinguishable, due to their smaller size. Mold and higher fungi colonies are distinguishable from the desired organisms because they are filamentous, whereas the desired organisms are non-filamentous. Clear or white-colored colonies can be picked from the plates and restreaked on a new plate of similar media composition. While most of the desired organisms are clear or white-colored, some are orange or red-colored due to the presence of xanthophyll pigments and are also suitable for selection and restreaking. The new plate can be incubated under similar conditions, preferably at 30° C. and single colonies picked after a 2–4 day incubation period. Single colonies can then be picked and placed in, for example, 50 ml of liquid medium containing the same organic enrichments (minus agar) as in the agar plates. These cultures can be incubated for 2–4 days at 30° C. with aeration, for example, on a rotary shaker table (100–200 rpm.). When the cultures appear to reach maximal density, 20–40 ml of the culture can then be harvested by centrifugation or other suitable method and preserved, as by lyophilization. The sample can then be analyzed by standard, well-known techniques including gas chromatography techniques to identify the fatty acid content of the strain. Those strains with omega-3 highly unsaturated fatty acids can thereby be identified and cultures of these strains maintained for further screening.

Promising strains can be screened for temperature tolerance by inoculating the strains into 250 ml shaker flasks containing 50 ml of culture media. These cultures are then incubated for 2 days on the shaker table over any desired temperature range from most practically between 27°–48° C., one culture at each 3° C. interval. Production can be quantified as the total amount of fatty acids produced per ml of culture medium. Total fatty acids can be quantified by gas chromatography as described above. A similar process can also be employed to screen for salinity tolerance. For salinity tolerance a range of salinities yielding conductivities from 5–40 mmho/cm is adequate for most purposes. Screening for the ability to utilize a variety of carbon and nitrogen sources can also be conducted employing the procedure outlined above. The carbon and nitrogen sources were evaluated herein at concentrations of 5 g/l. Carbon sources evaluated were: glucose, corn starch, ground corn, potato starch, wheat starch, and molasses. Nitrogen sources evaluated were: nitrate, urea, ammonium, amino acids, protein hydrolysate, corn steep liquor, tryptone, peptone, or casein. Other carbon and nitrogen sources can be used, the choice being open to those of ordinary skill in the art, based on criteria of significance to the user.

Using the collection and screening process, strains of unicellular microflora can be isolated which have fatty acid contents up to about 45% total cellular dry weight percent (% dwt), and which exhibit growth over a temperature range from 15–48° C. and grow in a very low salinity culture medium. Many of the very high omega-3 strains are very slow growers. Strains which have been isolated by the method outlined above, and which exhibit rapid growth, good production and high omega-3 HUFA content, have omega-3 unsaturated fatty acid contents up to approximately 12% dwt.

One aspect of the present invention is the growth of Thraustochytrium, Schizochytrium, and mixtures thereof with high omega-3 HUFA content, in fermentation medium containing non-chloride containing sodium salts and preferably sodium sulfate. More particularly, a significant portion of the sodium requirements of the fermentation are supplied as non-chloride containing sodium salts. For example, less than about 75% of the sodium in the fermentation medium is supplied as sodium chloride, more preferably less than about 50% and more preferably less than about 25%. A particular advantage of the present invention is that the medium provides the source of sodium needed by the microflora to grow in the absence of a significant amount of chloride which can corrode the vessel in which the microflora are being grown and other fermentation or downstream processing equipment. It has been surprisingly found that microflora of the present invention can be grown at chloride concentrations of less than about 3 gl/l, more preferably less than about 500 mg/l, more preferably less than about 250 mg/l and more preferably between about 60 mg/l and about 120 mg/l while still attaining high yields of biomass per sugar of about 50% or greater. As discussed below, an additional advantage of the present invention is the production of microflora that are high in omega-3 HUFA content but have a small enough cell aggregate size to be consumed by larval shrimp, brine shrimp, rotifers and mollusks.

Non-chloride containing sodium salts can include soda ash (a mixture of sodium carbonate and sodium oxide), sodium carbonate, sodium bicarbonate, sodium sulfate and mixtures thereof, and preferably include sodium sulfate. Soda ash, sodium carbonate and sodium bicarbonate tend to increase the pH of the fermentation medium, thus requiring control steps to maintain the proper pH of the medium. The concentration of sodium sulfate is effective to meet the salinity requirements of the microflora, preferably the sodium concentration is (expressed as g/l of Na) is greater than about 1.0 g/l, more preferably between about 1.0 g/l and about 50.0 g/l and more preferably between about 2.0 g/l and about 25 g/l.

It has been surprisingly found that fermentation of the strains in the presence of a non-chloride containing sodium salt and particularly, sodium sulfate limits the cell aggregate size of the strains to less than about 150 microns, preferably less than about 100 microns, and more preferably less than about 50 microns. As used herein, the term cell aggregate size refers to the approximate average diameter of clumps or aggregates of cells in a fermentation medium of a microfloral culture. Typically, greater than about 25 percent of the cell aggregates in a microfloral culture have cell aggregate size below the average size, more preferably greater than about 50 percent and more preferably greater than about 75 percent. Microfloral cells produced in accordance with the present invention meet cell aggregate size parameters described above while in fermentation medium as well as after freezing and/or drying of the biomass if resuspended in liquid or physically agitated, such as by a blender or vortexer. The present process is particularly important for microflora which replicate by successive bipartition (wherein a single cell replicates by dividing into two cells which each divide into two more, etc.) because as cells repeatedly and rapidly undergo this process, the cells tend to clump forming multi-cell aggregates which are often outside the cell aggregate size parameters identified above. Schizochytrium replicate by successive bipartition and by forming sporangia which release zoospores. Thraustochytrium, however, replicate only by forming sporangia and releasing zoospores. For Thraustochytrium which replicate by sporangia/zoospore formation, clumping can be a problem as well, particularly because even though the number of cells in an aggregate may not be as great as aggregates formed by successive bipartition, the individual cell sizes of Thraustochytrium tend to be larger, and thus, clumps of a small number of cells are larger. However, one deposited strain of Thraustochytrium, ATCC 26185, has been identified which does not exhibit significant aggregation.

In another aspect of the present invention, it has been found that by restricting the oxygen content of the fermentation medium during the growth of Thraustochytrium, Schizochytrium, and mixtures thereof, the lipid content of the strains can be increased. The optimum oxygen concentration for lipid production can be determined for any particular microflora by variation of the oxygen content of the medium. In particular, the oxygen content of the fermentation medium is maintained at an oxygen content of less than about 40% of saturation and preferably between about 5% of saturation and about 40% of saturation.

Growth of the strains by the invention process can be effected at any temperature conducive to satisfactory growth of the strains; for example, between about 5° C. and about 48° C., preferably between about 15° C. and about 40° C., and more preferably between about 25° C. and about 35° C. The culture medium typically becomes more alkaline during the fermentation if pH is not controlled by acid addition or buffers. The strains will grow over a pH range from 5.0–11.0 with a preferable range of about 6.0–8.5.

Various fermentation parameters for inoculating, growing and recovering microflora are discussed in detail in U.S. Pat. No. 5,130,242. The biomass harvested from a fermentation run can be dried (e.g., spray drying, tunnel drying, vacuum drying, or a similar process) and used as a feed or food supplement for any animal whose meat or products are consumed by humans. Similarly, extracted omega-3 HUFAs can be used as a feed or food supplement. Alternatively, the harvested and washed biomass can be used directly (without drying) as a feed supplement. To extend its shelf life, the wet biomass can be acidified (approximate pH =3.5–4.5) and/or pasteurized or flash heated to inactivate enzymes and then canned, bottled or packaged under a vacuum or non-oxidizing atmosphere (e.g., $N_2$ or $CO_2$). The term "animal means any organism belonging to the kingdom Animalia and includes, without limitation, any animal from which poultry meat, seafood, beef, pork or lamb is derived. Seafood is derived from, without limitation, fish, shrimp and shellfish. The term "products" includes any product other than meat derived from such animals, including, without limitation, eggs or other products. When fed to such animals, omega-3 HUFAs in the harvested biomass or extracted omega-3 HUFAs are incorporated into the flesh, eggs or other products of such animals to increase the omega-3 HUFA content thereof.

A further embodiment of the present invention is the use of the harvested biomass as a food product for larval shrimp, brine shrimp, rotifers and mollusks and in particular, larval shrimp. During the larval stage of development, shrimp larvae are unable to use some food sources because the food source is too large. In particular, at certain stages of development, shrimp larvae are unable to use a food source having a diameter greater than about 150 microns. Thus, microflora grown in fermentation medium containing a non-chloride sodium salt, and particularly sodium sulfate, as broadly discussed above, are suitable for use as a shrimp food product. As discussed above, microflora grown under such conditions typically have a cell aggregate size less than about 150 microns, preferably less than about 100 microns, and more preferably less than about 50 microns.

A further advantage of the use of microflora of the present invention as a food source for shrimp is that such microflora have a significant sterol content including cholesterol, which is a primary feed requirement for shrimp. The microflora of the present invention typically have a sterol content of preferably at least about 0.1% ash-free dry weight (afdw), more preferably at least about 0.5% afdw, and even more preferably at least about 1.0% afdw. In addition, the microflora of the present invention typically have a cholesterol content of preferably at least about 15% of the total sterol content, more preferably at least about 25% of the total sterol content, and even more preferably at least about 40% of the total sterol content. Further, the microfloral biomass of the present invention also provide shrimp with additional nutritional requirements such as omega-6 fatty acids, protein, carbohydrates, pigments and vitamins.

The microbial product of the present invention is of value as a source of omega-3 HUFAs for fish, shrimp and other products produced by aquaculture. The product can be used as a food product as described above for shrimp; or added directly as a supplement to the feed for shrimp and fish, generally; or it can be fed to brine shrimp or other live feed organisms intended for consumption by an aquacultured organism. The use of such microflora in this manner enables the shrimp farmer to obtain significantly higher growth rates and/or survival rates for larval shrimp and to produce post-larval shrimp which are more hardy and robust.

For most feed applications, the fatty acid content of the harvested cells will be approximately 15–50% dwt with the remaining material being largely protein and carbohydrate. The protein can contribute significantly to the nutritional value of the cells as several of the strains that have been evaluated have all of the essential amino acids and would be considered a nutritionally balanced protein.

A further embodiment of the present invention is the production of a food product using the Thraustochytrium, Schizochytrium, and mixtures thereof, of the present invention, combined with an additional component selected from the group consisting of rapeseed, flaxseed, soybean and avocado meal. A particular advantage of this embodiment is that the food product contains both short chain omega-3 HUFAs from the additional component and long chain omega-3 HUFAs from the microflora. Food products having flaxseed, rapeseed, soybeans and avocado meal are known to be useful for supplying a source of short chain omega-3 HUFAs and for additionally supplying a source of short chain omega-3 HUFAs, which can be elongated by the humans and animals that ingest them. Such food products, however, have the disadvantages of having high choline contents from the additional component, which can form primary amines and result in an unpleasant fish smell; and toxic compounds from the additional component, which at high levels can, for example, inhibit the laying of eggs by hens or cause animals to go off of their feed. As such, the food product of the present invention has the advantage of a lowered flaxseed, rapeseed, soy bean or avocado meal content because the organism ingesting the food product does not need high levels of short chain omega-3 HUFAs for the purpose of converting them to long chain HUFAs. Thus, the lowered content of the flaxseed and rapeseed of the food product results in lowered amounts of choline and/or inhibitory toxic compounds present in the food product.

The amount of Thraustochytrium, Schizochytrium, and mixtures thereof, used in the food product can range from between about 5% to about 95% by weight. The additional component can be present in the food product at a range of between about 5% to about 95% by weight. Additionally, the food product can include other components as well, including grains, supplements, vitamins, binders and preservatives.

In a preferred embodiment, the above food product is produced using an extrusion process. The extrusion process involves mixing the microflora with the additional component, thereby reducing the moisture in the microfloral biomass by the amount of the additional component mixed. The food product is extruded under heat, thus removing further moisture from the food product. The resulting product which has a low moisture content can be air dried or dried by relatively short baking times thereby reducing the overall energy requirements of drying and the potential degradation of omega-3 HUFAs due to long time periods at high temperatures. In addition, heat from the extrusion process can degrade some of the unwanted toxic compounds commonly found in the additional component which can, for example, inhibit egg laying by hens or cause animals to go off of their feed.

The present invention will be described in more detail by way of working examples. Species meeting the selection criteria described above have not been described in the prior art. By employing these selection criteria, over 25 potentially promising strains have been isolated from approximately 1000 samples screened. Out of the approximate 20,500 strains in the American Type Culture Collection (ATCC), 10 strains were later identified as belonging to the same taxonomic group as the strains isolated. Those strains still viable in the Collection were procured and used to compare with strains isolated and cultured by the disclosed procedures. The results of this comparison are presented in Examples 4 and 5 below.

The most recent taxonomic theorists place Thraustochydrids with the algae or algae-like protists. All of the strains of unicellular microorganisms disclosed and claimed herein are members of the order Thraustochytriales (Order: Thraustochytriales; Family: Thraustochytriaceae; Genus: Thraustochytrium or Schizochytrium). For general purposes of discussion herein, these microorganisms will be called microflora to better denote their uncertain exact taxonomic position.

The novel strains identified below were deposited under the Budapest Treaty on the International Recognition of the Deposit of Microorganisms for the Purpose of Patent Procedure. All restrictions on the availability to the public of the materials so deposited will be irrevocably removed upon the granting of a patent. Each deposit will be stored for a period of at least five years after the most recent request for the furnishing of a sample of the deposited microorganism is received by the American Type Culture Collection (ATCC), and, in any case, for a period of at least 30 years after the date of the deposit.

Preferred microorganisms of the present invention have all of the identifying characteristics of the deposited strains and, in particular, the identifying characteristics of being able to produce omega-3 HUFAs as described herein and having cell aggregate size characteristics when cultured under conditions as described herein. In particular, the preferred microorganisms of the present invention refer to the following deposited microorganisms and mutants thereof.

| Strain | ATCC No. | Deposit Date |
| --- | --- | --- |
| Schizochytrium S31 | 20888 | 8/8/88 |
| Schizochytrium S8 | 20889 | 8/B/88 |

The present invention, while disclosed in terms of specific organism strains, is intended to include all such methods and strains obtainable and useful according to the teachings disclosed herein, including all such substitutions, modification, and optimizations as would be available expedients to those of ordinary skill in the art.

The following examples and test results are provided for the purposes of illustration and are not intended to limit the scope of the invention.

EXAMPLES

Example 1

Collection and Screening

A 150 ml water sample was collected from a shallow, inland saline pond and stored in a sterile polyethylene bottle. Special effort was made to include some of the living plant material and naturally occurring detritus (decaying plant and animal matter) along with the water sample. The sample was placed on ice until return to the laboratory. In the lab, the water sample was shaken for 15–30 seconds, and 1–10 ml of the sample was pipetted or poured into a filter unit containing 2 types of filters: 1) on top, a sterile 47 mm diameter Whatman #4 filter having a pore size about 25 $\mu$m; and 2) underneath the Whatman filter, a 47 mm diameter polycarbonate filter with about 1.0 $\mu$m pore size. Given slight variations of nominal pore sizes for the filters, the cells collected on the polycarbonate filter range in size from about 1.0 $\mu$m to about 25 $\mu$m.

The Whatman filter was removed and discarded. The polycarbonate filter was placed on solid F-1 media in a petri plate, said media consisting of (per liter): 600 ml seawater (artificial seawater can be used), 400 ml distilled water, 10 g agar, 1 g glucose, 1 g protein hydrolysate, 0.2 g yeast extract, 2 ml 0.1 M $KH_2PO_4$, 1 ml of a vitamin solution (A-vits) (Containing 100 mg/l thiamine, 0.5 mg/l biotin, and 0.5 mg/l cyanocobalamin), 5 ml of a trace metal mixture (PII metals, containing per liter: 6.0 g $Na_2EDTA$, 0.29 g $FeCl_3 6H_2O$, 6.84 g $H_3BO_3$, 0.86 $MnCl_2 4H_2O$, 0.06 g $ZnCl_2$, 0.026 g $CoCl_2 6H_2O$, (0.052 g $NiSO_4H_2O$, 0.002 g $CuSo_4 5H_2O$, and 0.005 g $Na_2MoO_4 2H_2O$, and 500 mg each of streptomycin sulfate and penicillin-G. The agar plate was incubated in the dark at 30° C. After 2–4 days numerous colonies appeared on the filter. Colonies of unicellular microflora (except yeast) were picked from the plate and restreaked on a new plate of similar media composition. Special attention was made to pick all colonies consisting of colorless white cells. The new plate was incubated at 30° C. and single colonies picked after a 2–4 day incubation period. Single colonies were then picked and placed in 50 ml of liquid medium containing the same organic enrichments as in the agar plates. These cultures were incubated for 2–4 days at 30° C. on a rotary shaker table (100–200 rpm). When the cultures appeared to reach maximal density, 20–40 ml of the culture was harvested, centrifuged and lyophilized. The sample was then analyzed by standard, well-known gas chromatographic techniques (e.g., Lepage and Roy, 1984) to identify the fatty acid content of the strain. Those strains with omega-3 HUFAs were thereby identified, and cultures of these strains were maintained for further screening.

Using the collection and screening process outlined above, over 150 strains of unicellular microflora have been isolated which have high omega-3 HUFA contents as a percent of total fatty acids and which exhibit growth over a temperature range from 15–48° C. Strains can also be isolated which have less than 1% (as % of total fatty acids) of the undesirable C20:4n-6 and C22:5n-6 HUFAs for some applications. Strains with high omega-6 content can also be isolated. Strains of these microflora can be repeatedly isolated from the same location using the procedure outlined above. A few of the newly isolated strains have very similar fatty acid profiles. The possibility that some are duplicate isolates of the same strain cannot be ruled out at present. Further screening for other desirable traits such as salinity tolerance or ability to use a variety of carbon and nitrogen sources can then be carried out using a similar process.

Example 2

Maintaining Unrestricted Growth: $PO_4$ and Yeast Extract

Cells of *Schizochytrium aggregatum* (ATCC 28209) were picked from solid F-1 medium and inoculated into 50 ml of FFM medium. (Fuller et al., 1964). This medium contains: seawater, 1000 ml; glucose, 1.0 g; gelatin hydrolysate, 1.0 g; liver extract, 0.01 g; yeast extract, 0.1 g; PII metals, 5 ml; 1 ml B-vitamins solution (Goldstein et al., 1969); and 1 ml of an antibiotic solution (25 g/l streptomycin sulfate and penicillin-G). 1.0 ml of the vitamin mix (pH 7.2) contains: thiamine HCl, 200 $\mu$g; biotin, 0.5 $\mu$g; cyanocobalamin, 0.05 $\mu$g; nicotinic acid, 100 $\mu$g; calcium pantothenate, 100 $\mu$g; riboflavin, 5.0 $\mu$g; pyridoxine HCl, 40.0 $\mu$g; pyridoxamine 2HCl, 20.0 $\mu$g; p-aminobenzoic acid, 10 $\mu$g; chlorine HCl, 500 $\mu$g; inositol, 1.0 mg; thymine, 0.8 mg; orotic acid, 0.26 mg; folinic acid, 0.2 $\mu$g; and folic acid, 2.5 $\mu$g. The culture was placed on a rotary shaker (200 rpm) at 27° C. After 3–4 days, 1 ml of this culture was transferred to 50 ml of each of the following treatments: 1) FFM medium (as control); and 2) FFM medium with the addition of 250 mg/l $KH_2PO_4$ and 250 mg/l yeast extract. These cultures were placed on a rotary shaker (200 rpm) at 27° C. for 48 hr. The cells were harvested and the yield of cells quantified. In treatment 1, the final concentration of cells on an ash-free dry weight basis was 616 mg/l. In treatment 2, the final concentration of cells was 1675 mg/l, demonstrating the enhanced effect of increasing $PO_4$ and yeast extract concentrations in the culture medium.

Example 3

Maintaining Unrestricted Growth: Substitution of Corn Steep Liquor for Yeast Extract Cells of Schizochytrium sp. S31 (ATCC No. 20888) were picked from solid F-1 medium and placed into 50 ml of M-5 medium. This medium consists of (on a per liter basis): yeast extract, 1 g; NaCl, 25 g; $MgSO_4.7H_2O$, 5 g; KCl, 1 g; $CaCl_2$, 200 mg; glucose, 5 g; glutamate, 5 g; $KH_2PO_4$, 1 g; PII metals, 5 ml; A-vitamins solution, 1 ml; and antibiotic solution, 1 ml. The pH of the solution was adjusted to 7.0 and the solution was filter sterilized. Sterile solutions of corn steep liquor (4 g/40 ml; pH 7.0) and yeast extract (1 g/40 ml; pH 7.0) were prepared. To one set of M-5 medium flasks, the following amount of yeast extract solution was added: 1) 2 ml; 2) 1.5 ml; 3) 1 ml; 4) 0.5 ml; and 5) 0.25 ml. To another set of M-5 medium flasks the yeast extract and corn steep liquor solutions were added at the following levels: 1) 2 ml yeast extract; 2) 1.5 ml yeast extract and 0.5 ml corn steep liquor; 3) 1.0 ml yeast extract and 1.0 ml corn steep liquor; 4) 0.5 ml yeast extract and 1.5 ml corn steep liquor; and 5) 2 ml corn steep liquor. One ml of the culture in F-1 medium was used to inoculate each flask. They were placed on a rotary shaker at 27° C. for 48 hr. The cells were harvested by centrifugation and the yield of cells (as ash-free dry weight) was determined. The results are shown in Table 1. The results indicate the addition of yeast extract up to 0.8 g/l of medium can increase the yield of cells. However, addition of corn steep liquor is even more effective and results in twice the yield of treatments with added yeast extract. This is very advantageous for the economic production of cells as corn steep liquor is much less expensive than yeast extract.

TABLE 1

| Treatment (Amount Nutrient Supplement Added) | Ash-Free Dry weight (mg/l) |
|---|---|
| 2.0 ml yeast ext. | 4000 |
| 1.5 ml yeast ext. | 4420 |
| 1.0 ml yeast ext. | 4300 |
| 0.5 ml yeast ext. | 2780 |
| 0.25 ml yeast ext. | 2700 |
| 2.0 ml yeast ext. | 4420 |
| 1.5 ml yeast ext. + 0.5 ml CSL* | 6560 |
| 1.0 ml yeast ext. + 1.0 ml CSL | 6640 |
| 0.5 ml yeast ext. + 1.5 ml CSL | 7200 |
| 2.0 ml CSL | 7590 |

*CSL = corn steep liquor

Example 4
Enhanced HUFA Content of Strains Isolated by Method in Example 1 Compared to ATCC Strains (Previously Known Strains)

A battery of 151 newly isolated strains, selected according to the method described in Example 1, were sampled in late exponential phase growth and quantitatively analyzed for HUFA content by gas-liquid chromatography. All strains were grown either in M1 medium or liquid FFM medium, whichever gave highest yield of cells. M1 medium has the same composition as M5 medium, except that the concentrations of glucose and glutamate are 1 g/l. Additionally, five previously isolated Thraustochytrium or Schizochytrium species were obtained from the American Type Culture Collection, representing all the strains which could be obtained in viable form from the collection. These strains were: *T. aureum* (ATCC No. 28211), *T. aureum* (ATCC No. 34304), *T. roseum* (ATCC No. 28210), *T. straitum* (ATCC No. 34473) and *S. aggregatum* (ATCC No. 28209). The strains all exhibited abbreviated growth in conventional media, and generally showed improved growth in media of the present invention, including M5 medium and FFM medium. The fatty acid production of each of the known strains was measured as described, based upon the improved growth of the strains in media of the invention.

Fatty acid peaks were identified by the use of pure compounds of known structure. Quantitation, in terms of percent by weight of total fatty acids, was carried out by integrating the chromatographic peaks. Compounds identified were: palmitic acid (C16:0), C20:4n-6 and C22:1 (which were not resolved separately by the system employed), C20:5n-3, C22:5n-6, C22:5n-3, and C22:6n-3. The remainder, usually lower molecular weight fatty acids, were included in the combined category of "other fatty acids." Total omega-3 fatty acids were calculated as the sum of 20:5n-3, 22:5n-3 and 22:6n-3. Total omega-6 fatty acids were calculated as the sum of the 20:4/22:1 peak and the 22:5n-6 peak.

Figure 2:
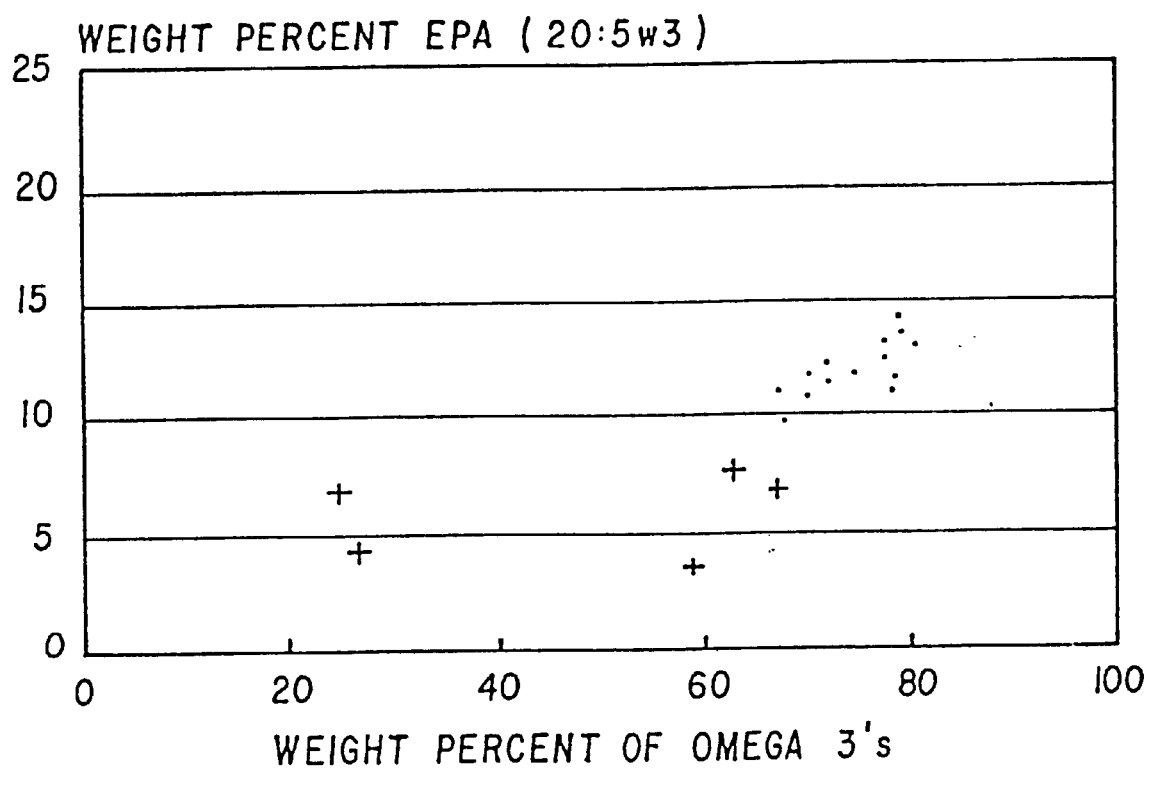
FIG. 2 is a graphical representation of HUFA production in newly isolated strains of the invention, represented by ■, and previously isolated strains, represented by +. Each point represents a strain, the position of each point is determined by the percent by weight of total fatty acids which were omega-3 HUFAs (abscissa) and percent of weight of total fatty acids which were eicosapentaenoic acid (EPA C20:5n-3) (ordinate). Only those strains of the invention were plotted wherein more than 67% (w/w) of total fatty acids were omega-3 and more than 7.8% (w/w) of total fatty acids were C20:5n-3.
Figure 3:
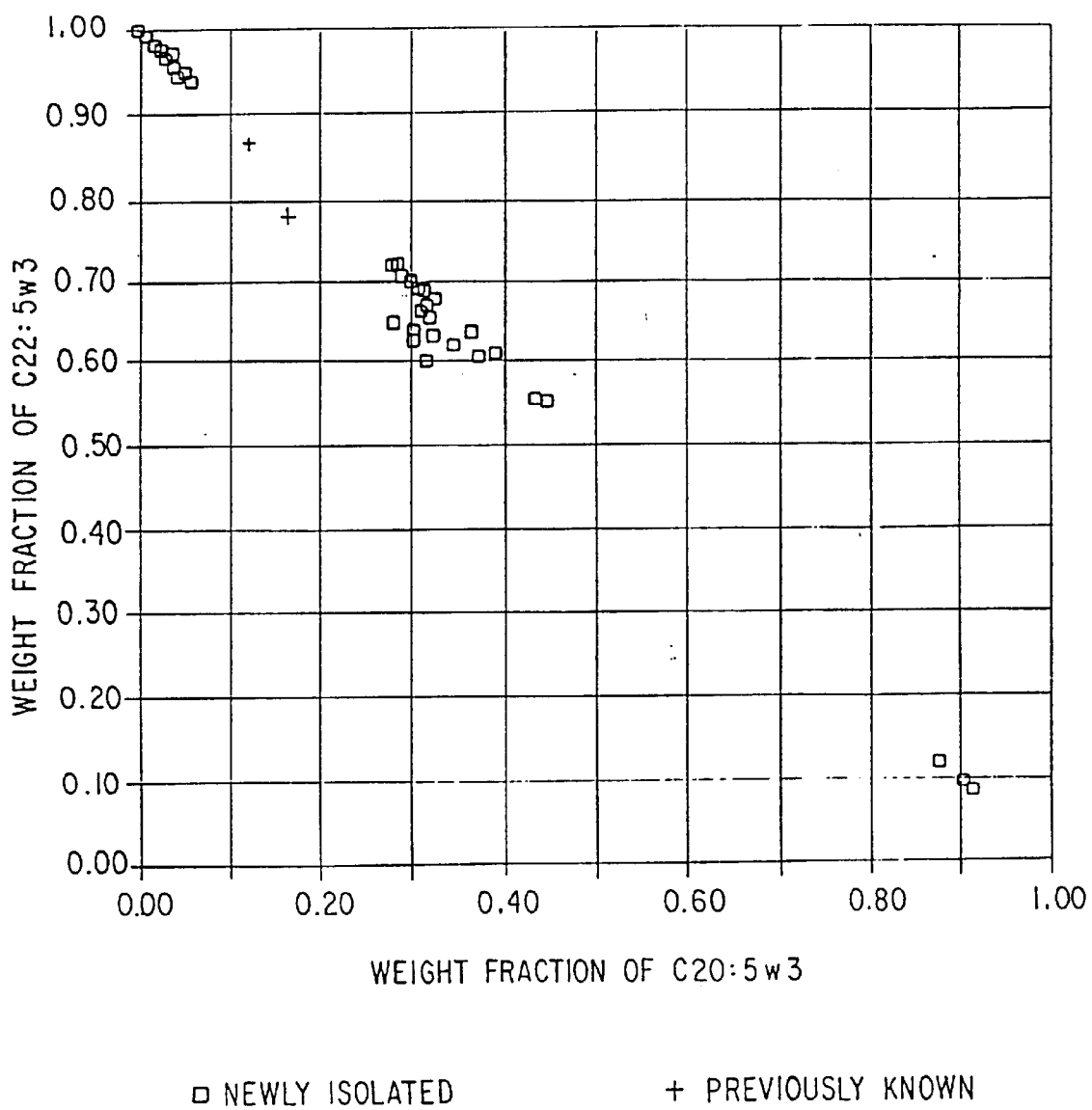
FIG. 3 is a graphical representation of omega-3 HUFA composition in newly isolated strains of the invention, represented by □, and previously isolated strains, represented by +. Each point represents a separate strain. Values on the abscissa are weight fraction of total omega-3 HUFAs which were C20:5n-3 and on the ordinate are weight fraction of total omega-3 fatty highly unsaturated acids which were C22:6n-3. Only strains of the invention were plotted having either a weight fraction of C20:5n-3 28% or greater, or a weight fraction of C22:6n-3 greater than 93.6%.

The results are shown in Tables 2–3 and illustrated in FIGS. 1–3. From Table 2 it can be seen that large numbers of strains can be isolated by the method of the invention, and that large numbers of strains outperform the previously known strains by several important criteria. For example, 102 strains produced at least 7.8% by weight of total fatty acids C20:5w3, a higher percentage of that fatty acid than any previously known strain. Strains 23B (ATCC No. 20892) and 12B (ATCC No. 20890) are examples of such strains. Thirty (30) strains of the invention produced at least 68% by weight of total fatty acids as omega-3 fatty acids, more than any previously known strain. Strain 23B (ATCC No. 20892) is an example of such strains. Seventy-six (76) strains of the invention yielded not more than 10% by weight of total fatty acids as omega-6 fatty acids, considered undesirable components of the human diet, lower than any previously known strain. Strains 23B (ATCC No. 20892) and 12B (ATCC No. 20890) are examples of such strains. In addition, there are 35 strains of the invention that produce more than 25% by weight of total fatty acids as omega-6 fatty acids, more than any previously known strain. While such strains may have a more narrow range of uses for dietary purposes, they are useful as feedstock for chemical synthesis of eicosanoids starting from omega-6 fatty acids.

In addition, the data reveal many strains of the invention which produce a high proportion of total omega-3 fatty acids as C22:6n-3. In Table 3, 48 of the strains shown in Table 2 were compared to the previously known strains, showing each of C20:5n-3, C22:5n-3 and C22:6n-3 as percent by weight of total omega-3 content. Fifteen strains had at least 94% by weight of total omega-3 fatty acids as C22:6n-3, more than any previously known strain. Strain S8 (ATCC No. 20889) was an example of such strains. Eighteen strains had at least 28% by weight of total omega-3 fatty acids as C20:5n-3, more than any previously known strain. Strain 12B (ATCC No. 20890) was an example of such strains.

TABLE 2

LIST OF STRAINS AND COMPOSITIONS UNDER STANDARD SCREENING CONDITIONS

| PERCENT OF TOTAL FATTY ACIDS | | | | | | | Total | Total | |
|---|---|---|---|---|---|---|---|---|---|
| C16:0 | C20:4w6 | C20:5w3 | C22:5w6 | C22:5w3 | C22.6w3 | Other FA | Omega 3 | Omega 6 | Strain |
| 30.4% | 2.8% | 6.6% | 3.2% | 0.2% | 8.3% | 48.5% | 15.1% | 6.0% | 21 |
| 22.9% | 0.4% | 2.3% | 15.5% | 0.5% | 47.0% | 11.5% | 49.7% | 15.9% | ATCC 20889 |
| 14.9% | 6.5% | 12.0% | 11.8% | 0.4% | 49.7% | 4.7% | 62.1% | 18.3% | U40-2 |
| 40.3% | 1.7% | 3.8% | 8.6% | 0.0% | 8.2% | 37.4% | 12.0% | 10.2% | 21B |
| 20.7% | 0.4% | 7.8% | 0.0% | 0.0% | 1.1% | 70.1% | 8.9% | 0.4% | BG1 |
| 26.0% | 5.7% | 1.5% | 9.7% | 0.7% | 9.7% | 46.7% | 11.9% | 15.4% | 56A |
| 16.4% | 1.4% | 10.0% | 1.9% | 2.2% | 46.4% | 21.8% | 58.6% | 3.3% | 11A-1 |
| 23.7% | 3.3% | 10.5% | 1.9% | 1.8% | 29.9% | 28.9% | 42.2% | 5.2% | 4A-1 |
| 18.7% | 6.9% | 9.2% | 11.9% | 3.2% | 25.2% | 24.9% | 37.5% | 18.8% | 17B |
| 15.4% | 4.2% | 7.3% | 9.5% | 0.9% | 51.2% | 11.6% | 59.3% | 13.7% | ATCC 20891 |
| 22.3% | 3.9% | 7.6% | 23.5% | 0.5% | 22.1% | 20.2% | 30.2% | 27.4% | S44 |
| 14.4% | 2.3% | 15.0% | 18.4% | 0.7% | 43.8% | 5.5% | 59.4% | 20.7% | U30 |
| 22.1% | 7.8% | 3.1% | 12.7% | 1.0% | 14.9% | 38.3% | 19.0% | 20.5% | 59A |
| 18.1% | 2.3% | 6.9% | 9.1% | 0.8% | 52.2% | 10.6% | 59.9% | 11.4% | U37-2 |

TABLE 2-continued

LIST OF STRAINS AND COMPOSITIONS UNDER STANDARD SCREENING CONDITIONS

| PERCENT OF TOTAL FATTY ACIDS | | | | | | | Total | Total | |
|---|---|---|---|---|---|---|---|---|---|
| C16:0 | C20:4w6 | C20:5w3 | C22:5w6 | C22:5w3 | C22:6w3 | Other FA | Omega 3 | Omega 6 | Strain |
| 15.8% | 3.9% | 8.8% | 11.6% | 1.2% | 53.3% | 5.5% | 63.3% | 15.5% | S50W |
| 23.7% | 3.8% | 6.3% | 6.9% | 0.6% | 43.0% | 15.6% | 50.0% | 10.7% | ATCC 20891 |
| 10.0% | 0.0% | 0.0% | 0.0% | 0.0% | 0.0% | 90.0% | 0.0% | 0.0% | UX |
| 16.6% | 6.3% | 11.9% | 13.3% | 1.7% | 43.0% | 7.3% | 56.6% | 19.5% | LW9 |
| 17.3% | 2.3% | 8.4% | 11.4% | 0.7% | 53.6% | 6.5% | 62.6% | 13.6% | C32-2 |
| 23.8% | 1.2% | 6.4% | 2.5% | 1.9% | 34.4% | 29.8% | 42.6% | 3.7% | 5A-1 |
| 17.1% | 5.2% | 11.1% | 7.6% | 2.2% | 27.2% | 29.6% | 40.4% | 12.9% | BG1 |
| 25.4% | 2.2% | 9.6% | 7.0% | 1.1% | 46.0% | 8.8% | 56.7% | 9.1% | U3 |
| 16.9% | 12.0% | 6.6% | 16.2% | 0.4% | 25.1% | 22.8% | 32.1% | 28.2% | 55B |
| 26.3% | 2.6% | 8.6% | 2.0% | 2.5% | 32.4% | 25.5% | 43.5% | 4.6% | 18A |
| 19.4% | 0.3% | 9.8% | 0.0% | 0.3% | 38.4% | 31.7% | 48.6% | 0.3% | 32B |
| 16.0% | 16.7% | 8.6% | 18.4% | 0.0% | 22.5% | 17.7% | 31.1% | 35.1% | 56B |
| 18.6% | 7.7% | 11.4% | 3.6% | 4.3% | 31.7% | 22.7% | 47.4% | 11.2% | SX2 |
| 17.8% | 4.4% | 16.2% | 6.4% | 3.7% | 33.6% | 17.8% | 53.5% | 10.9% | S3B |
| 16.8% | 2.7% | 13.8% | 20.5% | 1.4% | 39.3% | 5.5% | 54.4% | 23.3% | S49 |
| 20.8% | 8.0% | 8.9% | 6.4% | 1.7% | 33.9% | 20.3% | 44.5% | 14.4% | S3 |
| 14.8% | 0.3% | 3.7% | 3.9% | 0.0% | 69.9% | 7.4% | 73.6% | 4.2% | 3A-1 |
| 28.1% | 5.2% | 12.7% | 3.2% | 0.9% | 20.9% | 29.0% | 34.5% | 8.4% | 15A |
| 20.9% | 0.7% | 8.5% | 1.0% | 0.0% | 35.8% | 33.0% | 44.3% | 1.7% | 9A-1 |
| 15.7% | 10.2% | 8.8% | 13.4% | 1.5% | 23.9% | 26.3% | 34.3% | 23.7% | 51B |
| 16.2% | 11.2% | 7.8% | 16.4% | 1.5% | 20.4% | 26.5% | 29.7% | 27.6% | 8A-1 |
| 20.5% | 5.5% | 8.6% | 4.8% | 2.7% | 28.7% | 29.2% | 40.0% | 10.3% | 13A-I |
| 16.1% | 13.6% | 11.1% | 16.0% | 0.0% | 28.4% | 14.8% | 39.4% | 29.6% | 24B-2 |
| 16.9% | 7.3% | 16.4% | 6.1% | 0.0% | 40.8% | 12.4% | 57.2% | 13.4% | 24B-1 |
| 16.2% | 0.0% | 10.9% | 1.0% | 0.0% | 56.5% | 15.5% | 67.4% | 1.0% | 3B |
| 17.0% | 0.0% | 5.0% | 2.3% | 0.0% | 73.4% | 2.3% | 78.3% | 2.3% | SBG5 |
| 20.8% | 4.5% | 5.8% | 3.8% | 1.0% | 22.7% | 41.3% | 29.5% | 8.4% | 16B |
| 19.0% | 14.0% | 8.3% | 18.9% | 0.7% | 23.9% | 15.2% | 32.9% | 32.9% | 6A-1 |
| 18.0% | 0.3% | 10.1% | 0.0% | 0.0% | 48.9% | 22.7% | 59.0% | 0.3% | 33B |
| 16.7% | 5.5% | 14.8% | 8.5% | 1.7% | 31.8% | 21.0% | 48.3% | 13.9% | B40 |
| 15.0% | 1.0% | 11.7% | 2.1% | 0.9% | 62.3% | 6.9% | 74.9% | 3.1% | 28A |
| 17.8% | 18.5% | 8.1% | 20.5% | 0.0% | 22.1% | 12.9% | 30.2% | 39.0% | 43B |
| 16.9% | 0.0% | 3.4% | 2.7% | 0.0% | 61.2% | 15.8% | 64.6% | 2.7% | 1A-l |
| 15.6% | 2.7% | 11.4% | 10.9% | 0.8% | 53.7% | 4.9% | 65.9% | 13.6% | U41-2 |
| 16.5% | 0.7% | 3.9% | 3.9% | 0.0% | 68.4% | 6.7% | 72.2% | 4.6% | 56B |
| 14.4% | 0.9% | 10.9% | 2.5% | 1.0% | 66.4% | 3.8% | 78.3% | 3.4% | 46A |
| 17.6% | 0.0% | 2.4% | 3.3% | 0.0% | 66.3% | 10.4% | 68.7% | 3.3% | 15A-1 |
| 25.0% | 0.0% | 3.3% | 0.0% | 1.4% | 53.2% | 17.1% | 57.9% | 0.0% | 13A |
| 16.1% | 13.4% | 9.3% | 13.6% | 0.0% | 32.3% | 15.3% | 41.6% | 27.0% | 37B |
| 16.5% | 9.1% | 13.2% | 6.7% | 0.0% | 38.9% | 15.6% | 52.1% | 15.9% | 43B |
| 16.1% | 12.4% | 12.0% | 15.7% | 0.8% | 30.5% | 12.5% | 43.3% | 28.1% | 17B |
| 13.8% | 0.8% | 11.5% | 2.8% | 0.0% | 67.0% | 4.1% | 78.6% | 3.6% | 27A |
| 17.5% | 18.6% | 9.0% | 19.5% | 0.0% | 21.7% | 13.7% | 30.7% | 38.1% | 46B |
| 21.4% | 1.4% | 18.9% | 0.0% | 5.0% | 43.5% | 9.9% | 67.3% | 1.4% | ATCC 20890 |
| 17.7% | 0.0% | 0.6% | 4.4% | 0.0% | 68.2% | 9.1% | 68.8% | 4.4% | 5A |
| 17.6% | 16.0% | 9.6% | 18.8% | 0.0% | 25.6% | 12.4% | 35.2% | 34.8% | 28B-2 |
| 14.0% | 0.9% | 13.2% | 1.6% | 0.0% | 64.7% | 5.5% | 77.9% | 2.6% | 27B |
| 19.5% | 2.9% | 16.6% | 1.1% | 1.6% | 30.2% | 28.1% | 48.5% | 4.0% | 49B |
| 17.2% | 0.7% | 6.8% | 2.7% | 0.0% | 63.0% | 9.6% | 69.8% | 3.4% | 18B |
| 14.4% | 3.5% | 13.5% | 26.0% | 1.0% | 37.2% | 4.4% | 51.6% | 29.5% | S49-2 |
| 16.1% | 2.2% | 15.7% | 21.6% | 0.0% | 36.7% | 7.8% | 52.4% | 23.7% | 20B |
| 17.3% | 4.7% | 14.3% | 7.2% | 2.9% | 30.2% | 23.5% | 47.3% | 11.9% | 8B |
| 11.5% | 3.3% | 11.3% | 6.5% | 1.1% | 59.9% | 6.5% | 72.2% | 9.8% | 13B |
| 16.6% | 0.7% | 10.7% | 1.6% | 0.0% | 59.7% | 10.8% | 70.4% | 2.2% | 26A |
| 16.1% | 3.3% | 13.5% | 23.8% | 0.0% | 38.7% | 4.7% | 52.2% | 27.1% | S42 |
| 15.6% | 0.6% | 12.1% | 0.0% | 0.0% | 60.2% | 11.5% | 72.3% | 0.6% | 35B |
| 19.5% | 0.0% | 1.4% | 3.4% | 0.0% | 66.6% | 9.1% | 68.0% | 3.4% | 42A |
| 18.9% | 3.5% | 12.7% | 25.0% | 0.0% | 35.0% | 5.0% | 47.6% | 28.5% | 40A |
| 25.2% | 3.3% | 9.3% | 21.8% | 0.0% | 30.3% | 10.1% | 39.6% | 25.1% | S50C |
| 17.6% | 11.1% | 13.2% | 14.1% | 1.3% | 28.7% | 14.0% | 43.2% | 25.2% | 59A |
| 19.9% | 0.0% | 5.5% | 1.9% | 0.0% | 66.8% | 6.0% | 72.3% | 1.9% | SBG9 |
| 15.4% | 3.1% | 13.2% | 26.1% | 0.0% | 35.8% | 6.5% | 49.1% | 29.1% | 21B |
| 18.9% | 0.7% | 11.6% | 0.0% | 0.0% | 59.1% | 9.7% | 70.7% | 0.7% | 2B |
| 14.1% | 1.1% | 12.4% | 2.0% | 0.0% | 65.2% | 5.2% | 77.6% | 3.1% | 1B |
| 22.2% | 16.2% | 6.3% | 17.7% | 0.0% | 18.1% | 19.5% | 24.4% | 33.8% | 55B |
| 16.0% | 1.0% | 4.5% | 0.0% | 0.0% | 69.5% | 9.0% | 74.0% | 1.0% | 3A |
| 17.0% | 4.3% | 12.4% | 29.8% | 0.0% | 34.0% | 2.5% | 46.4% | 34.1% | 9B |
| 15.4% | 4.3% | 8.7% | 13.2% | 0.0% | 53.2% | 5.1% | 62.0% | 17.5% | U24 |
| 14.2% | 3.1% | 12.0% | 20.0% | 1.1% | 35.2% | 14.3% | 48.3% | 23.2% | U28 |
| 16.8% | 14.6% | 10.1% | 16.0% | 0.6% | 27.7% | 14.0% | 38.5% | 30.7% | 28B-1 |
| 23.2% | 1.9% | 8.3% | 1.1% | 2.3% | 22.7% | 40.4% | 33.3% | 3.0% | 44B |
| 24.6% | 15.8% | 8.7% | 16.0% | 0.0% | 15.3% | 19.6% | 24.0% | 31.8% | 54B |
| 15.5% | 0.0% | 1.3% | 2.9% | 0.0% | 72.7% | 7.6% | 74.0% | 2.9% | 55A |

TABLE 2-continued

LIST OF STRAINS AND COMPOSITIONS UNDER STANDARD SCREENING CONDITIONS

| PERCENT OF TOTAL FATTY ACIDS | | | | | | | Total | Total | |
|---|---|---|---|---|---|---|---|---|---|
| C16:0 | C20:4w6 | C20:5w3 | C22:5w6 | C22:5w3 | C22:6w3 | Other FA | Omega 3 | Omega 6 | Strain |
| 18.4% | 1.0% | 5.0% | 3.0% | 0.0% | 66.2% | 6.4% | 71.3% | 3.9% | 49A |
| 18.6% | 15.3% | 9.4% | 18.0% | 0.0% | 27.3% | 11.4% | 36.7% | 33.3% | 51A |
| 23.5% | 13.1% | 7.3% | 17.9% | 0.0% | 26.7% | 11.4% | 34.0% | 31.0% | 14A-1 |
| 13.3% | 1.1% | 14.5% | 0.9% | 0.0% | 64.6% | 5.6% | 79.1% | 2.0% | 25B |
| 22.9% | 2.4% | 10.3% | 21.5% | 0.0% | 26.5% | 16.4% | 36.9% | 23.9% | 41A |
| 16.8% | 1.0% | 9.7% | 2.7% | 0.0% | 58.3% | 11.5% | 68.0% | 3.7% | 24A |
| 0.4% | 8.5% | 14.1% | 10.2% | 2.1% | 27.6% | 37.0% | 43.8% | 18.8% | 61A |
| 30.5% | 0.0% | 7.1% | 0.0% | 0.0% | 0.6% | 61.8% | 7.7% | 0.0% | BRBG |
| 18.2% | 14.9% | 8.3% | 18.7% | 0.0% | 24.4% | 15.5% | 32.7% | 33.6% | 17A |
| 17.4% | 2.0% | 9.3% | 2.8% | 0.0% | 55.7% | 12.7% | 65.0% | 4.9% | 60A |
| 14.1% | 0.8% | 13.0% | 1.2% | 0.0% | 67.8% | 3.1% | 80.8% | 2.0% | 26B |
| 17.8% | 5.0% | 6.9% | 15.0% | 1.5% | 47.4% | 6.4% | 55.8% | 20.0% | ATCC 20888 |
| 16.0% | 0.0% | 1.8% | 2.0% | 0.0% | 70.8% | 9.4% | 72.6% | 2.0% | 2A |
| 24.6% | 0.0% | 4.0% | 0.0% | 0.0% | 49.4% | 22.0% | 53.4% | 0.0% | 44A |
| 17.4% | 1.8% | 0.0% | 2.9% | 0.0% | 55.3% | 23.3% | 55.3% | 4.6% | 14A |
| 23.3% | 1.3% | 4.6% | 0.0% | 0.0% | 12.6% | 58.1% | 17.3% | 1.3% | 41B |
| 19.3% | 0.0% | 1.1% | 3.8% | 0.0% | 66.7% | 9.1% | 67.8% | 3.8% | 66A |
| 18.6% | 15.6% | 8.3% | 17.1% | 1.1% | 24.6% | 14.8% | 33.9% | 32.7% | 11A |
| 19.6% | 5.1% | 10.1% | 27.2% | 0.0% | 27.5% | 10.6% | 37.5% | 32.3% | 2X |
| 15.7% | 2.4% | 14.0% | 25.7% | 0.0% | 36.7% | 5.4% | 50.8% | 28.1% | 33A |
| 14.6% | 1.5% | 13.5% | 0.0% | 0.0% | 66.0% | 4.3% | 79.5% | 1.5% | ATCC 20892 |

PRIOR STRAINS

| PERCENT OF TOTAL FATTY ACIDS | | | | | | | Total | Total | |
|---|---|---|---|---|---|---|---|---|---|
| C16:0 | C20:4w6 | C20:5w3 | C22:5w6 | C22:5w3 | C22:6w3 | Other FA | Omega 3 | Omega 6 | Strain |
| 15.7% | 3.9% | 3.7% | 8.1% | 0.0% | 55.1% | 13.5% | 58.8% | 12.0% | ATCC 34304 |
| 28.2% | 1.6% | 6.9% | 11.4% | 0.0% | 17.8% | 34.1% | 24.7% | 12.9% | ATCC 24473 |
| 15.2% | 2.9% | 7.7% | 9.8% | 0.6% | 54.6% | 9.2% | 62.9% | 12.7% | ATCC 28211 |
| 23.2% | 10.7% | 4.3% | 12.6% | 1.5% | 20.6% | 27.0% | 26.4% | 23.4% | ATCC 28209 |
| 13.2% | 6.3% | 6.9% | 4.3% | 0.0% | 60.1% | 9.1% | 67.0% | 10.6% | ATCC 28210 |

TABLE 3

COMPOSITION OF OMEGA 3 FATY ACID FRACTION

| EPA C202:5w3 | DPA C22:5w3 | DHA C22:6w3 | Strain |
|---|---|---|---|
| 44.0% | 1.1% | 54.9% | 21 |
| 4.6% | 0.9% | 94.5% | ATCC 20889 |
| 19.3% | 0.7% | 80.0% | U40-2 |
| 31.9% | 0.0% | 68.1% | 21B |
| 87.9% | 0.0% | 12.1% | BRBG1 |
| 12.5% | 6.1% | 81.5% | 56A |
| 17.0% | 3.7% | 79.3% | 11A-1 |
| 24.9% | 4.3% | 70.8% | 4A-1 |
| 24.4% | 8.4% | 67.2% | 17B |
| 12.2% | 1.5% | 86.3% | ATCC 20891 |
| 25.1% | 1.7% | 73.2 | S44 |
| 25.2% | 1.1% | 73.7% | U30 |
| 16.2% | 5.4% | 78.4% | 59A |
| 11.5% | 1.4% | 87.1% | U37-2 |
| 14.0% | 1.9% | 84.2% | S50W |
| 12.7% | 1.3% | 86.0% | ATCC 20891 |
| — | — | — | UX |
| 21.0% | 2.9% | 76.1% | LWN9 |
| 13.4% | 1.0% | 85.6% | C32-2 |
| 15.0% | 4.3% | 80.7% | SA-I |
| 27.4% | 5.4% | 67.2% | BRBG1 |
| 17.0% | 1.9% | 81.1% | U3 |
| 20.5% | 1.3% | 78.2% | 55B |
| 19.8% | 5.8% | 74.4% | 18A |
| 20.1% | 0.7% | 79.2% | 32B |
| 27.8% | 0.0% | 72.2% | 56B |
| 24.1% | 9.1% | 66.9% | SX2 |
| 30.3% | 6.9% | 62.8% | 53B |
| 25.3% | 2.5% | 72.2% | S49 |
| 19.9% | 3.8% | 76.3% | S3 |
| 5.0% | 0.0% | 95.0% | 3A-1 |
| 36.9% | 2.6% | 60.5% | 15A |
| 19.3% | 0.0% | 80.7% | 9A-1 |
| 25.8% | 4.4% | 69.8% | 51B |
| 26.3% | 5.0% | 68.7% | 8A-1 |
| 21.6% | 6.7% | 71.7% | 13A-1 |
| 28.0% | 0.0% | 72.0% | 24B-2 |
| 28.7% | 0.0% | 71.3% | 24B-1 |
| 16.2% | 0.0% | 83.8% | 3B |
| 6.3% | 0.0% | 93.7% | SBGS |
| 19.7% | 3.3% | 77.0% | 1GB |
| 25.2% | 2.1% | 72.6% | 6A-1 |
| 17.1% | 0.0% | 82.9% | 33B |
| 30.5% | 3.6% | 65.9% | B40 |
| 15.6% | 1.2% | 83.1% | 28A |
| 26.8% | 0.0% | 73.2% | 43B |

TABLE 3-continued

COMPOSITION OF OMEGA 3 FATY ACID FRACTION

| EPA C202:5w3 | DPA C22:5w3 | DHA C22:6w3 | Strain |
|---|---|---|---|
| 5.2% | 0.0% | 94.8% | 1A-1 |
| 17.4% | 1.2% | 81.5% | U41-2 |
| 5.4% | 0.0% | 94.6% | 56B |
| 13.9% | 1.3% | 84.8% | 46A |
| 3.5% | 0.0% | 96.5% | 16A-1 |
| 5.8% | 2.4% | 91.8% | 13A |
| 22.3% | 0.0% | 77.7% | 37B |
| 25.4% | 0.0% | 74.6% | 43B |
| 27.7% | 1.9% | 70.3% | 17B |
| 14.7% | 0.0% | 85.3% | 27A |
| 29.2% | 0.0% | 70.8% | 46B |
| 28.0% | 7.5% | 64.5% | ATCC 20890 |
| 0.9% | 0.0% | 99.1% | 5A |
| 27.3% | 0.0% | 72.7% | 288-1 |
| 16.9% | 0.0% | 83.1% | 27-B |
| 34.3% | 3.4% | 62.3% | 49B |
| 9.7% | 0.0% | 90.3% | 18B |
| 26.1% | 1.9% | 71.9% | S49-2 |
| 29.9% | 0.0% | 70.1% | 20B |
| 30.1% | 6.2% | 63.7% | 8B |
| 15.6% | 1.5% | 82.9% | 13B |
| 15.2% | 0.0% | 84.8% | 26A |
| 25.9% | 0.0% | 74.1% | S42 |
| 16.7% | 0.0% | 83.3% | 35B |
| 2.1% | 0.0% | 97.9% | 42A |
| 26.6% | 0.0% | 73.4% | 40A |
| 23.4% | 0.0% | 76.6% | S50C |
| 30.6% | 2.9% | 66.4% | 59A |
| 7.6% | 0.0% | 92.4% | SBG9 |
| 27.0% | 0.0% | 73.0% | 21B |
| 16.4% | 0.0% | 83.6% | 2B |
| 15.9% | 0.0% | 84.1% | 1B |
| 25.9% | 0.0% | 74.1% | 55B |
| 6.0% | 0.0% | 94.0% | 3A |
| 26.7% | 0.0% | 73.3% | 9B |
| 14.1% | 0.0% | 85.9% | U24 |
| 24.9% | 2.2% | 72.9% | U28 |
| 26.4% | 1.5% | 72.1% | 28B-1 |
| 24.8% | 6.9% | 68.3% | 44B |
| 36.4% | 0.0% | 63.6% | 54B |
| 1.8% | 0.0% | 98.2% | 55A |
| 7.1% | 0.0% | 92.9% | 49A |
| 25.6% | 0.0% | 74.4% | 51A |
| 21.5% | 0.0% | 78.5% | 14A-1 |
| 18.4% | 0.0% | 81.6% | 25B |
| 28.1% | 0.0% | 71.9% | 41A |
| 14.3% | 0.0% | 85.7% | 24A |
| 32.3% | 4.8% | 63.0% | 61A |
| 91.6% | 0.0% | 8.4% | BRBG |
| 25.5% | 0.0% | 74.5% | 17A |
| 14.4% | 0.0% | 85.6% | 60A |
| 16.1% | 0.0% | 83.9% | 26B |
| 12.4% | 2.7% | 84.9% | ATCC 20888 |
| 2.5% | 0.0% | 97.5% | 2A |
| 7.5% | 0.0% | 92.5% | 44A |
| 0.0% | 0.0% | 100.0% | 14A |
| 26.7% | 0.0% | 73.3% | 41B |
| 1.7% | 0.0% | 98.3% | 66A |
| 24.5% | 3.1% | 72.4% | 11A |
| 26.8% | 0.0% | 73.2% | 2X |
| 27.6% | 0.0% | 72.4% | 33A |
| 17.0% | 0.0% | 83.0% | ATCC 20892 |
| PRIOR STRAINS | | | |
| 6.4% | 0.0% | 93.6% | ATCC 34304 |
| 27.9% | 0.0% | 72.1% | ATCC Z4473 |
| 12.2% | 1.0% | 86.8% | ATCC 28211 |
| 16.4% | 5.6% | 78.1% | ATCC 28209 |
| 10.3% | 0.0% | 89.7% | ATCC 28210 |

FIG. 1 illustrates the set of strains, isolated by the method in Example 1, that have more than 67% omega-3 fatty acids (as % of total fatty acids) and less than 10.6% omega-6 fatty acids (as % of total fatty acids). All of the previously known strains had less than 67% omega-3 fatty acids (as % of total fatty acids) and greater than 10.6% omega-6 (as % of total fatty acids).

FIG. 2 illustrates the set of strains, isolated by the method in Example 1, that have more than 67% omega-3 fatty acids (as % of total fatty acids) and greater than 7.5% C20:5n-3 (as % of total fatty acids). All of the previously known strains had less than 67% omega-3 fatty acids (as % of total fatty acids) and less than 7.8% C20:5n-3 (as % of total fatty acids).

Example 5

Enhanced Growth Rates of Strains Isolated by Method in Example 1 Compared to ATCC Strains (Previously Known Strains)

Figure 4:
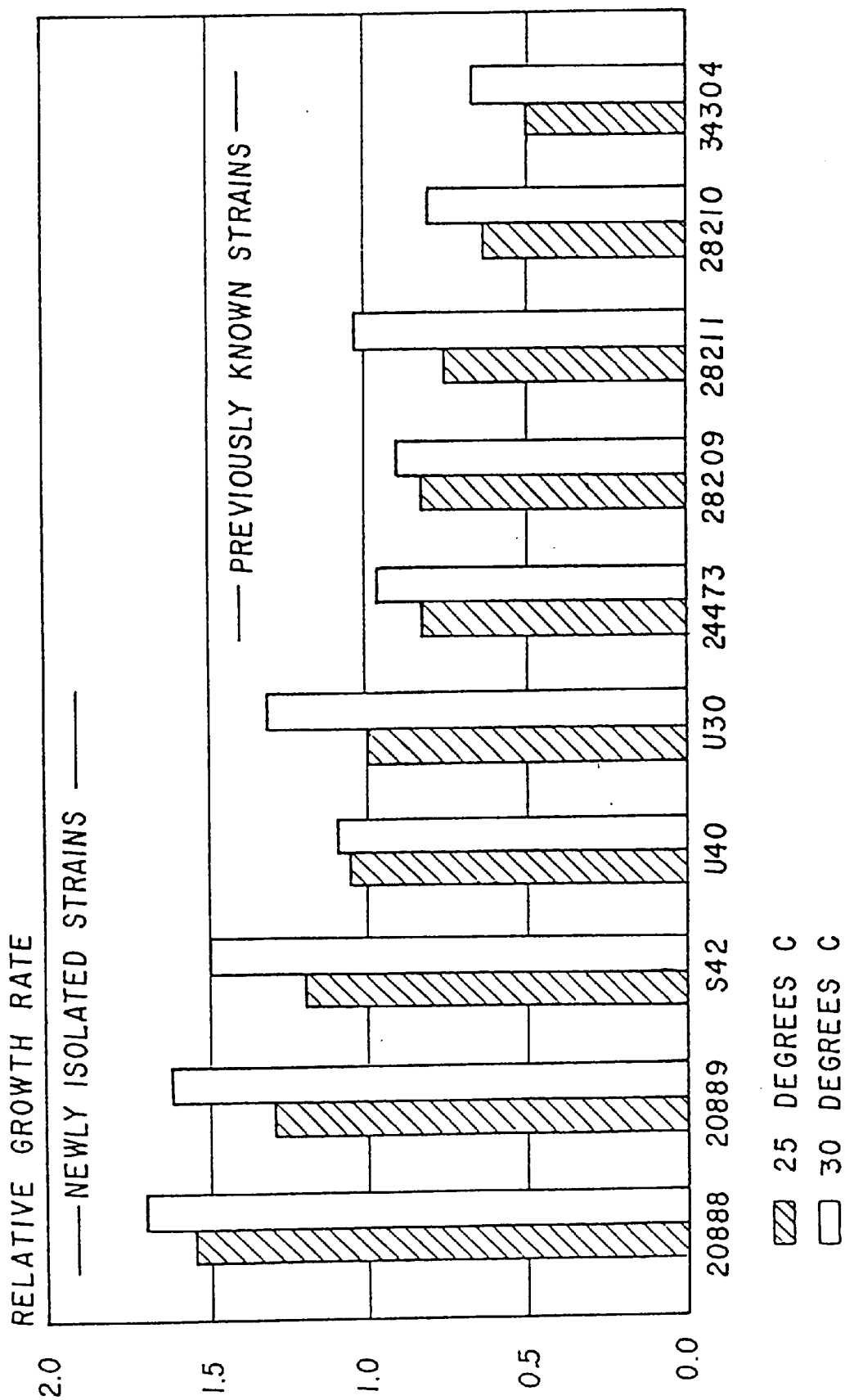
FIG. 4 is a graph showing growth of various newly isolated strains of the invention and previously isolated strains, at 25° C. and at 30° C. Growth rates are normalized to the growth rate of strain U-30 at 25° C. Previously isolated strains are designated by their ATCC accession numbers.

Cells of Schizochytrium sp. S31 (ATCC No. 20888), Schizochytrium sp. S8 (ATCC No. 20889), Thraustochytrium sp. S42, Thraustochytrium sp. U42-2, Thraustochytrium sp. S42 and U30, (all isolated by the method of Example 1) and Thraustochytrium aureum (ATCC #28211) and Schizochytrium aggregatum (ATCC #28209) (previously known strains) were picked from solid F-1 medium and placed into 50 ml of M-5 medium. The pH of the solution was adjusted to 7.0 and the solution was filter sterilized. After three days of growth on an orbital shaker (200 rpm, 27° C.), 1–2 ml of each culture was transferred to another flask of M-5 medium and placed on the shaker for 2 days. The cultures (1–2 ml) were then transferred to another flask of M-5 medium and placed on the shaker for 1 day. This process ensured that all cultures were in the exponential phase of growth. These later cultures were then used to inoculate two 250 ml flasks of M-5 medium for each strain. These flasks were than placed on shakers at 25° C. and 30° C., and changes in their optical density were monitored on a Beckman DB-G spectrophotometer (660 nm, 1 cm path length). Optical density readings were taken at the following times: 0, 6, 10, 14, 17.25, 20.25 and 22.75 hours. Exponential growth rates (doublings/day) were then calculated from the optical density data by the method of Sorokin (1973). The results are presented in Table 4 and illustrated (normalized to the growth of strain U30 at 25° C.) in FIG. 4. The data indicate that the strains isolated by the method in Example 1 have much higher growth rates than the previously known ATCC strains at both 25° C. and 30° C., even under the optimized phosphate levels essential for continuous growth. Strains of Thraustochytriales isolated from cold Antarctic waters have not been shown to grow at 30° C.

TABLE 4

Exponential Growth Rate (doublings/day)

| Strain | 25° C. | 30° C. |
|---|---|---|
| S31* (ATCC No. 20888) | 8.5 | 9.4 |
| U40-2* | 5.8 | 6.0 |
| S8* (ATCC No. 20889) | 7.1 | 8.8 |
| S42* | 6.6 | 8.3 |
| U30* | 5.5 | 7.3 |
| 28209** | 4.6 | 5.0 |
| 28210** | 3.5 | 4.5 |
| 28211** | 4.2 | 5.7 |
| 34304** | 2.7 | 3.7 |
| 24473** | 4.6 | 5.3 |

*strain isolated by method in Example 1
**previously known ATCC strain

Example 6
Enhanced Production Characteristics (Growth and Lipid Induction) of Strains Isolated by Method in Example 1 Compared to ATCC Strains (Prior Art Strains)

Figure 5:
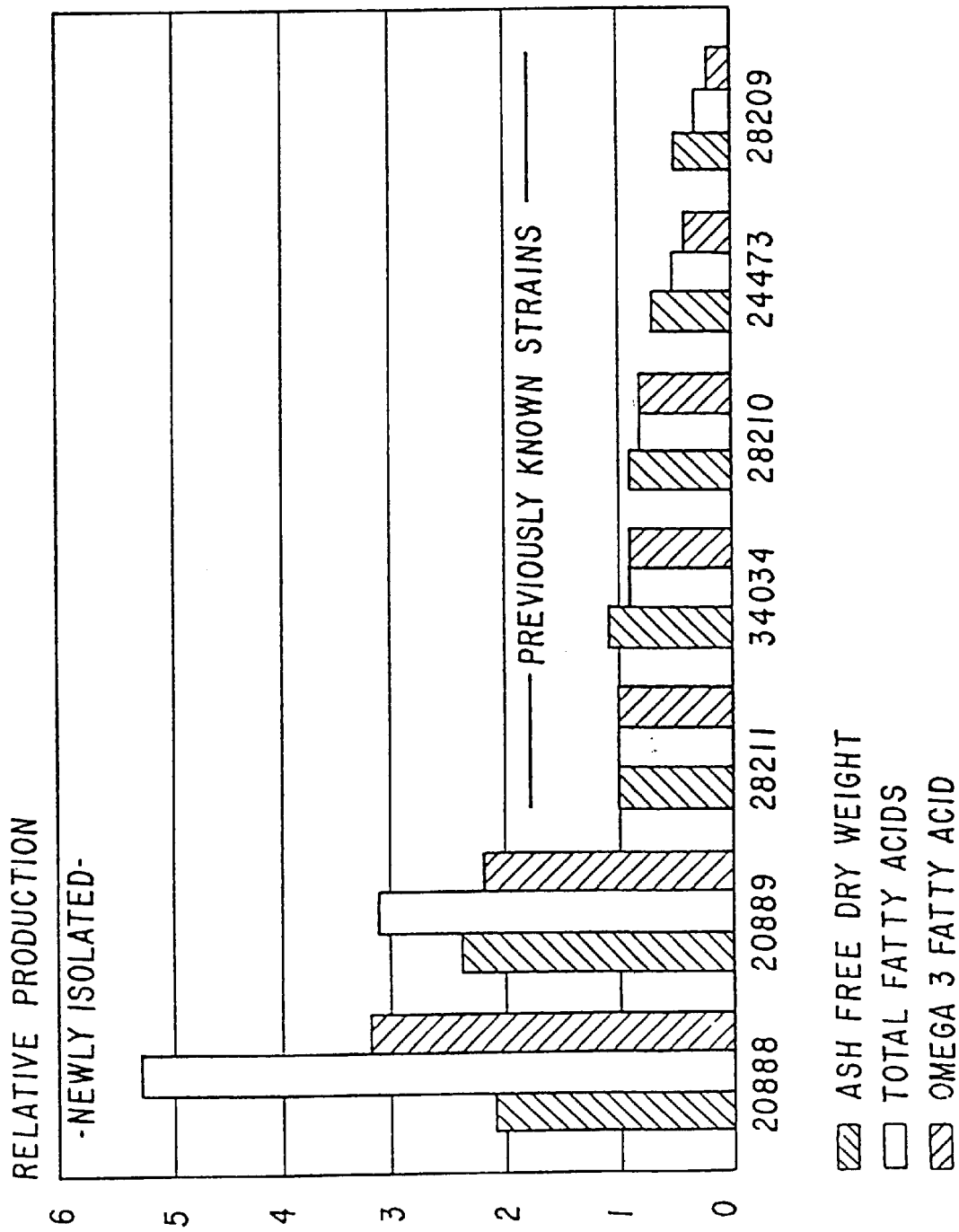
FIG. 5 is a graph of total yields of cellular production after induction by nitrogen limitation. Each of ash-free dry weight, total fatty acids and omega-3 HUFAs, as indicated, was plotted, normalized to the corresponding value for strain 28211. All strains are identified by ATCC accession numbers.

Cells of Schizochytrium sp. S31 (ATCC No. 20888), Schizochytrium sp. S8 (ATCC No. 20889) (both isolated by the method of Example 1) and *Thraustochytrium aureum* (ATCC #28211) and *Schizochytrium aggregatum* (ATCC #28209) (prior art strains) were picked from solid F-1 medium and placed into 50 ml of M-5 medium (see Example 3). The pH of the solution was adjusted to 7.0 and the solution was filter sterilized. After three days of growth on an orbital shaker (200 rpm, 27° C.), 1–2 ml of each culture was transferred to another flask of M-5 medium and placed on the shaker for 2 days. The ash-free dry weights for each of these cultures were the n quickly determined and then 3.29 mg of each culture was pipetted into two 250 ml erlenmeyer flasks containing 50 ml of M-5 medium. These flasks were placed on a rotary shaker (200 rpm, 270° C.). After 24 hours 20 ml portions of each culture were then centrifuged, the supernatants discarded, an d the cells transferred to 250 ml erlenmeyer flasks containing 50 ml of M-5 medium without any glutamate (N-source). The flasks were placed back on the shaker, and after another 12 hours they were sampled to determine ash-free dry weights and quantify fatty acid contents by the method of Lepage and Roy (1984). The results are illustrated (normalized to the yields of ATCC No.28211, previously known strain) in FIG. 5. The results indicate that the strains isolated by the method of Example 1 produced 2–3 times as much ash-free dry weight in the same period of time, under a combination of exponential growth and nitrogen limitation (for lipid induction) as the prior art ATCC strains. In addition, higher yields of total fatty acids and omega-3 fatty acids were obtained from strains of the present invention with strains S31 (ATCC No. 20888) producing 3–4 times as much omega-3 fatty acids as the prior art ATCC strains.

Example 7
Enhanced Lower Salinity Tolerance and Fatty Acid Production by Strains Isolated by Method in Example 1

Figure 6:
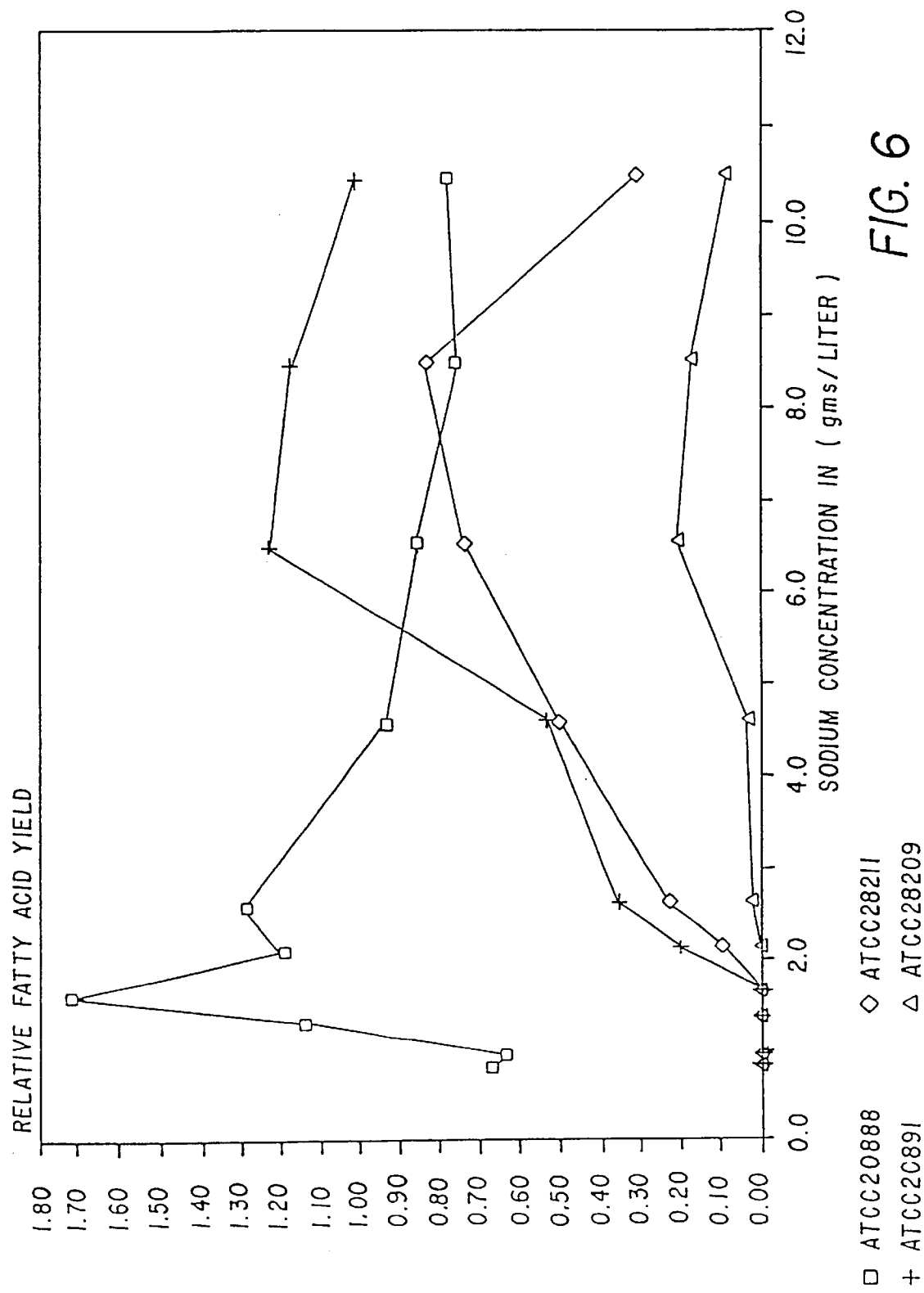
FIG. 6 is a graph of fatty acid yields after growth in culture media having the salinity indicated on the abscissa. Strains shown are newly isolated strains S31 (ATCC 20888) (□) and U42-2 (ATCC 20891) (+) and previously isolated strains, ATCC 28211 (◇) and ATCC 28209 (△). Fatty acid yields are plotted as relative yields normalized to an arbitrary value of 1.00 based on the average growth rate exhibited by S31 (ATCC 20888) (□) over the tested salinity range.

Strains of 4 species of Thraustochytrids, Schizochytrium Sp. S31 (ATCC No.20888) and Thraustochytrium sp. U42-2 (ATCC No. 20891) (both isolated and screened by the method of Example 1), and *S. aggregatum* (ATCC 28209) and *T. aureum* (ATCC 28210) (obtained from the American Type Culture Collection) were picked from solid F-1 medium and incubated for 3–4 days at 27° C. on a rotary shaker (200 rpm). A range of differing salinity medium was prepared by making the following dilutions of M medium salts (NaCl, 25 g/l; $MgSO_4.7H_2O$, 5 g/l; KCl, 1 g/l; $CaCl_2$, 200 mg/l: 1) 100% (w/v M medium salts; 2) 80% (v/v) M medium, 20% (v/v) distilled water; 3) 60% (v/v) M medium, 40% (v/v) distilled water; 4) 40% (v/v) M medium, 60% (v/v) distilled water; 5) 20% (v/v) M medium, 80% distilled water; 6) 15% (v/v) M medium, 85% (v/v) distilled water; 7) 10% (v/v) M medium, 90% (v/v) distilled water; 8) 7% (v/v) M medium, 93% (v/v) distilled water; 9) 3% (v/v) M medium, 97% (v/v) distilled water; 10) 1.5% (v/v) M medium, 98.5% (v/v) distilled water. The following nutrients were added to the treatments (per liter): glucose, 5 g; glutamate, 5 g; yeast ext., 1 g; $(NH_4)_2SO_4$, 200 mg; $NaHCO_3$, 200 mg; PII metals, 5 ml; A-vitamins solution, 1 ml; and antibiotics solution, 2 ml. Fifty ml of each of these treatments were inoculated with 1 ml of the cells growing in the F-1 medium. These cultures were placed on an orbital shaker (200 rpm) and maintained at 27° C. for 48 hr. The cells were harvested by centrifugation and total fatty acids determined by gas chromatography. The results are illustrated in FIG. 6. Thraustochytrium sp. U42-2 (ATCC No. 20891) isolated by the method of Example 1 can yield almost twice the amount of fatty acids produced by *T. aureum* (ATCC 28211) and over 8 times the amount of fatty acids produced by *S. aggregatum* (ATCC 28209). Additionally, U42-2 appears to have a wider salinity tolerance at the upper end of the salinity range evaluated. Schizochytrium sp. S31 (ATCC No. 20888), also isolated by the method in Example 1, exhibited both a high fatty acid yield (2.5 to 10 times that of the previously known ATCC strains) and a much wider range of salinity tolerance than the ATCC strains. Additionally, Schizochytrium sp. S31 (ATCC No. 20888) grows best at very low salinities. This property provides a strong economic advantage when considering commercial production, both because of the corrosive effects of saline waters on metal reactors, and because of problems associated with the disposal of saline waters.

Example 8
Cultivation/Low Salinity

Fifty ml of M/10-5 culture media in a 250 ml erlenmeyer flask was inoculated with a colony of Schizochytrium sp. S31 (ATCC No. 20888) picked from an agar slant. The M/10-5 media contains: 1000 ml deionized water, 2.5 g NaCl, 0.5 g $MgSO_4.7H_2O$, 0.1 g KCl, 0.02 g $CaCl_2$, 1.0 g $KH_2PO_4$, 1.0 g yeast extract, 5.0 g glucose, 5.0 glutamic acids, 0.2 g $NaHCO_3$, 5 ml PII trace metals, 2 ml vitamin mix, and 2 ml antibiotic mix. The culture was incubated at 30° C. on a rotary shaker (200 rpm). After 2 days the culture was at a moderate density and actively growing. 20 ml of this actively growing culture was used to inoculate a 2 liter fermenter containing 1700 ml of the same culture media except the concentration of the glucose and glutamate had been increased to 40 g/l (M/10-40 media). The fermenter was maintained at 30° C., with aeration at 1 vol/vol/min, and mixing at 300 rpm. After 48 hr, the concentration of cells in the fermenter was 21.7 g/l. The cells were harvested by centrifugation, lyophilized, and stored under $N_2$.

The total fatty acid content and omega-3 fatty acid content was determined by gas chromatography. The total fatty acid content of the final product was 39.0% ash-free dry weight. The omega-3 HUFA content (C20:5n-3, C22:5n-3 and C22:6n-3) of the microbial product was 25.6% of the total fatty acid content. The ash content of the sample was 7.0%.

Example 9
Diversity of Fatty Acid Content

Growth and gas chromatographic analysis of fatty acid production by various strains as described in Example 4 revealed differences in fatty acid diversity. Strains of the present invention synthesized fewer different fatty acids than previously available strains. Lower diversity of fatty acids is advantageous in fatty acid purification since there are fewer impurities to be separated. For food supplement purposes, fewer different fatty acids is advantageous because the likelihood of ingesting unwanted fatty acids is reduced. Table 5 shows the number of different HUFAs present, at concentrations greater than 1% by weight of total fatty acids for previously known strains, designated by ATCC number and various strains of the present invention.

TABLE 5

| Strain | No. of Different Fatty Acids at 1% or Greater % of Total Fatty Acids |
|---|---|
| 34304** | 8 |
| 28211** | 8 |
| 24473** | 10 |
| 28209** | 13 |
| 28210** | 8 |
| S31* | 5 |
| S8* | 6 |
| 79B* | 6 |

*strain isolated by the method in Example 1
**previously known ATCC strain

Example 10
Recovery

Fifty ml of M5 culture media in a 250 ml erlenmeyer flask was inoculated with a colony of Schizochytrium sp. S31 (ATCC No. 20888) picked from an agar slant. The culture was incubated at 30° C. on a rotary shaker (200 rpm). After 2 days the culture was at a moderate density and actively growing. 20 ml of this actively growing culture was used to inoculate a 1 liter fermenter containing 1000 ml of the same culture media except the concentration of the glucose and glutamate had been increased to 40 g/l (M20 media). The fermenter was maintained at 30° C. and pH 7.4, with aeration at 1 vol/min, and mixing at 400 rpm. After 48 hr, the concentration of the cells in the fermenter was 18.5 g/l. Aeration and mixing in the fermenter was turned off. Within 2–4 minutes, the cells flocculated and settled in the bottom 250 ml of the fermenter. This concentrated zone of cells had a cell concentration of 72 g/l. This zone of cells can be siphoned from the fermenter, and: (1) transferred to another reactor for a period of nitrogen limitation (e.g., combining the highly concentrated production of several fermenters); or (2) harvested directly by centrifugation or filtration. By preconcentrating the cells in this manner, 60–80% less water has to be processed to recover the cells.

Example 11
Utilization of a Variety of Carbon and Nitrogen Sources

Fifty ml of M5 culture media in a 250 ml erlenmeyer flask was inoculated with a colony of Schizochytrium sp. S31 (ATCC No. 20888) or Thraustochytrium sp. U42-2 (ATCC No. 20891) picked from an agar slant. The M5 media was described in Example 3 except for the addition of 2 ml vitamin mix, and 2 ml antibiotic mix. The culture was incubated at 30° C. on a rotary shaker (200 rpm). After 2 days the culture was at a moderate density and actively growing. This culture was used to inoculate flasks of M5 media with one of the following substituted for the glucose (at 5 g/l): dextrin, sorbitol, fructose, lactose, maltose, sucrose, corn starch, wheat starch, potato starch, ground corn; or one of the following substituted for the glutamate (at 5 g/l): gelysate, peptone, tryptone, casein, corn steep liquor, urea, nitrate, ammonium, whey, or corn gluten meal. The cultures were incubated for 48 hours on a rotary shaker (200 rpm, 27° C.). The relative culture densities, representing growth on the different organic substrates, are illustrated in Tables 6–7.

TABLE 6

Utilization of Nitrogen Sources

| | Strains | |
|---|---|---|
| N-Source | Thraustochytrium sp. U42-2 ATCC No. 20891 | Schizochytrium sp. S31 ATCC No. 20888 |
| glutamate | +++ | +++ |
| gelysate | +++ | +++ |
| peptone | ++ | ++ |
| tryptone | ++ | ++ |
| casein | ++ | ++ |
| corn steep liquor | +++ | +++ |
| urea | + | ++ |
| nitrate | ++ | +++ |
| ammonium | + | +++ |
| whey | +++ | +++ |
| corn gluten meal | +++ | +++ |

+++ = high growth
++ = medium growth
+ = low growth
0 = no growth

TABLE 7

Utilization of Organic Carbon Sources

| | Strains | |
|---|---|---|
| C-Source | Thraustochytrium sp. U42-2 ATCC No. 20891 | Schizochytrium sp. S31 ATCC No. 20888 |
| glucose | +++ | +++ |
| dextrin | +++ | +++ |
| sorbitol | + | + |
| fructose | + | +++ |
| lactose | + | + |
| maltose | +++ | + |
| sucrose | + | + |
| corn starch | +++ | + |
| wheat starch | +++ | + |
| potato starch | +++ | + |
| ground corn | +++ | 0 |

+++ = high growth
++ = medium growth
+ = low growth
0 = no growth

Figure 7:
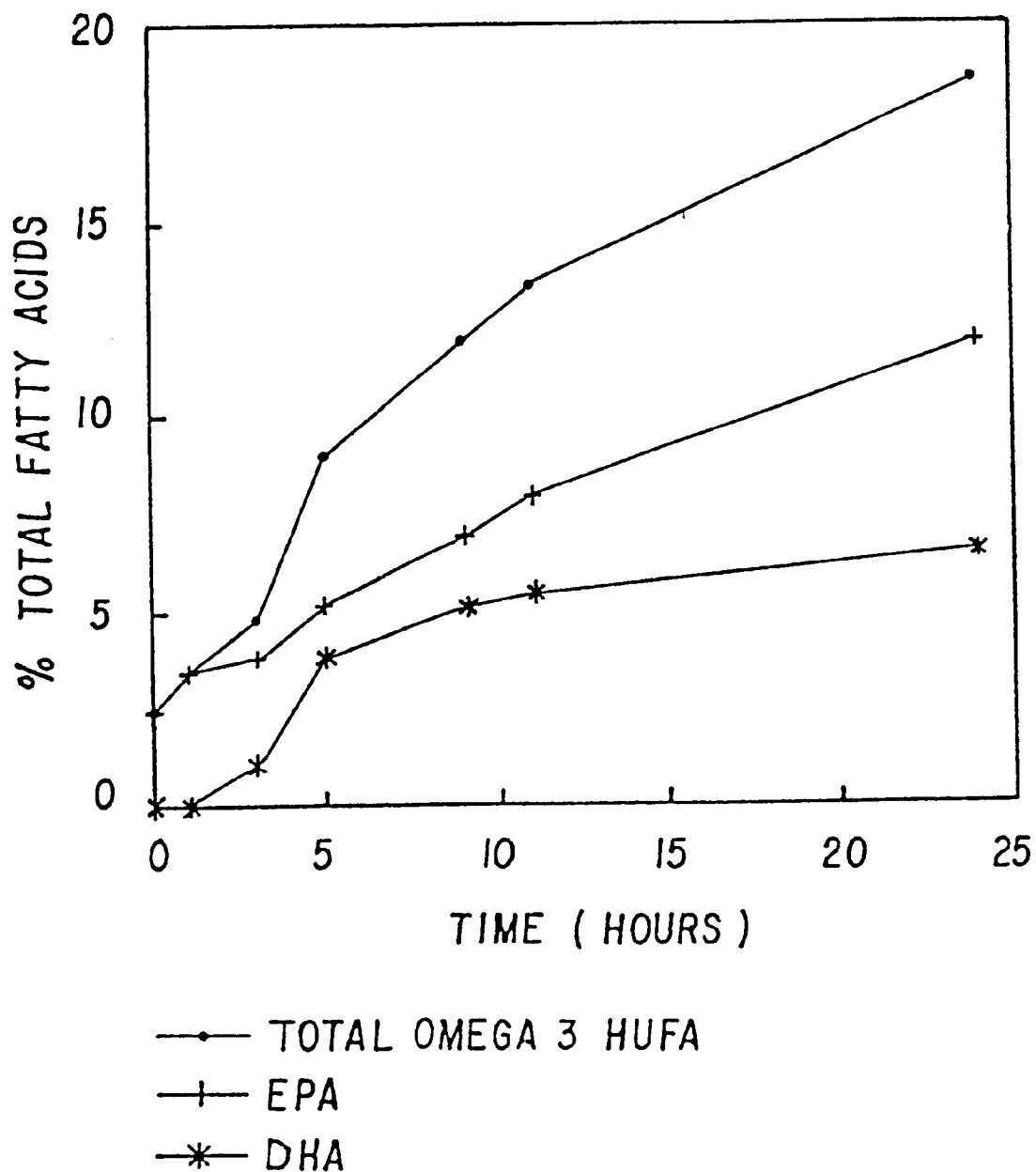
FIG. 7 is a graph of increases in the omega-3 HUFA content of the total lipids in the brine shrimp, *Artemia salina*, fed Thraustochytrid strain (ATCC 20890) isolated by the method in Example 1. EPA=C20:5n-3; DHA=C22:5n-3.
Figure 8:
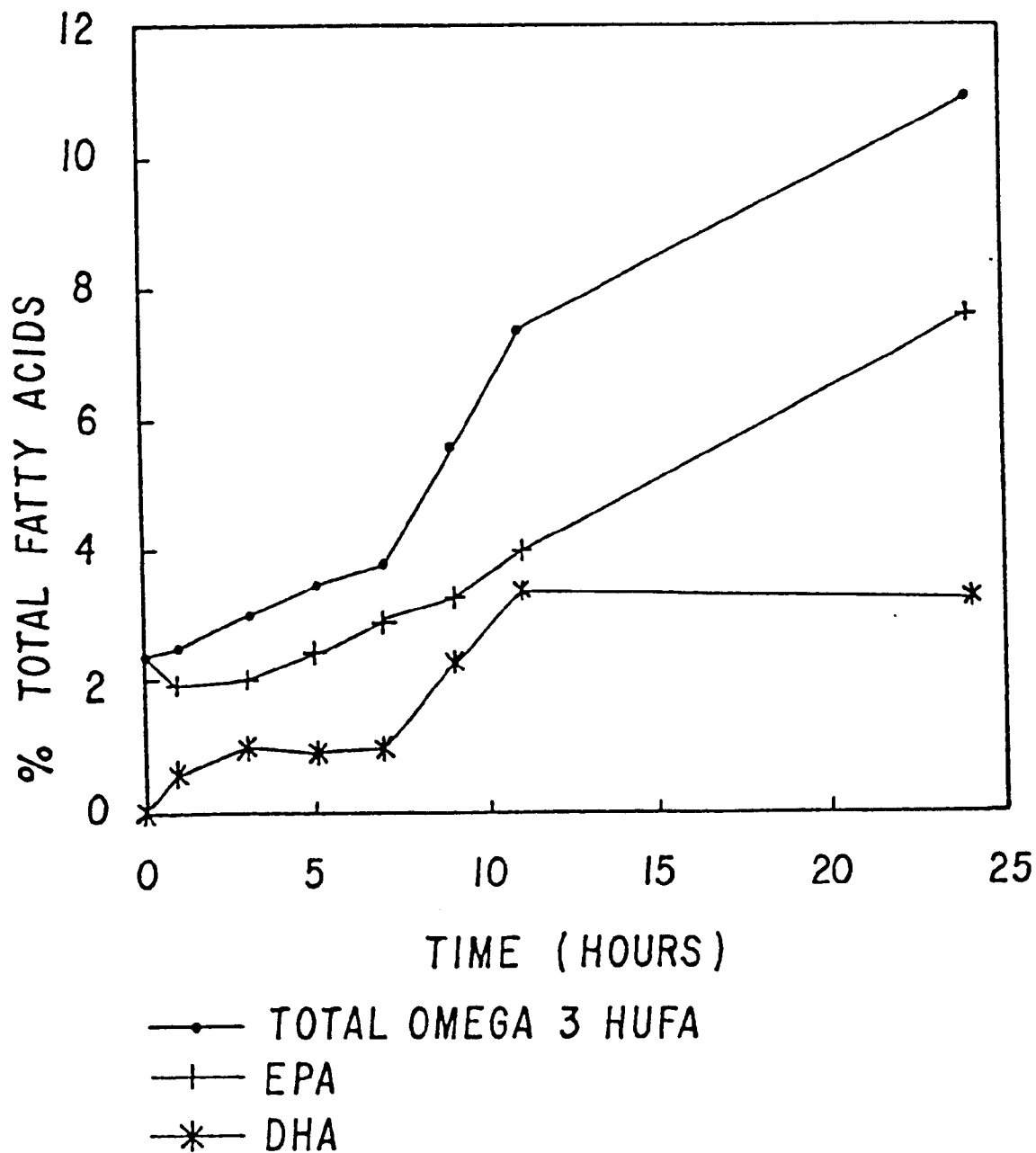
FIG. 8 is a graph of increases in the omega-3 HUFA content of the total lipids in the brine shrimp, *Artemia salina*, fed Thraustochytrid strain (ATCC 20888) isolated by the method in Example 1. EPA=C20:5n-3; DHA=C22:5n-3.

Example 12
Feeding of Thraustochytrid-Based Feed Supplement to Brine Shrimp to Increase Their Omega-3 HUFA Content Cellular biomass of Thraustochytrium sp. 12B (ATCC 20890) was produced in shake flasks in M-5 medium (see Example 3) at 25° C. Cellular biomass of Thraustochytrium sp. S31 (ATCC 20888) was produced in shake flasks in M/10-5 medium (see Example 8) at 27° C. The cells of each strain were harvested by centrifugation. The pellet was washed once with distilled water and recentrifuged to produce a 50% solids paste. The resulting paste was resuspended in sea water and then added to an adult brine shrimp culture as a feed supplement. The brine shrimp had previously been reared on agricultural waste products and as a result their omega-3 HUFA content was very low, only 1.3–2.3% of total fatty acids (wild-caught brine shrimp have an average omega-3 HUFA content of 6–8% total fatty acids). The brine shrimp (2–3/mL) were held in a 1 liter beaker filled with sea water and an airstone was utilized to aerate and mix the culture. After addition of the feed supplement, samples of the brine shrimp were periodically harvested, washed, and their fatty acid content determined by gas chromatography. The results are illustrated in FIGS. 7 and 8. When fed the thraustochytrid-based feed supplement as a finishing feed, the omega-3 content of the brine shrimp can be raised to that of wild-type brine shrimp within 5 hours if fed strain 12B or within 11 hours when fed strain S31. The omega-3 HUFA content of the brine shrimp can be greatly enhanced over that of the wild type if fed these feed supplements for up to 24 hours. Additionally, these feed supplements greatly increase the DHA content of the brine shrimp, which is generally only reported in trace levels in wild-caught brine shrimp.

Example 13
Use of Sodium Sulfate in Culture Medium

This example illustrates that omega-3 production and total fatty acid content is not harmed and can be the same or better when using sodium sulfate instead of sodium chloride as the sodium salt in a fermentation medium.

Schizochytrium ATCC No. 20888 was grown in medium, pH 7.0, containing 2.36 grams of sodium per liter of medium, 1.5–3.0 grams of a nitrogen source per liter of medium, and 3.0 grams of glucose per liter of medium. The cells were incubated at 28° C., at 200 rotations per minute, for 48 hours. The results are shown in Table 8.

TABLE 8

Effect of Sodium Sulfate Compared With Sodium Chloride on Fatty Acid Content

| N source (g/L) | omega-3 (% dwt) | total fatty acid (% dwt) | biomass yield (g/L) |
|---|---|---|---|
| A) Na salt = sodium chloride; N source = sodium glutamate | | | |
| 3.0 | 6.0 | 11.2 | 1.74 |
| 2.5 | 5.8 | 10.8 | 1.71 |
| 2.0 | 5.8 | 11.0 | 1.65 |
| 1.5 | 7.5 | 20.3 | 1.39 |
| B) Na salt = sodium chloride; N source = peptone | | | |
| 3.0 | 7.9 | 21.9 | 1.34 |
| 2.5 | 9.4 | 27.4 | 1.21 |
| 2.0 | 6.7 | 28.9 | 1.18 |
| 1.5 | 11.1 | 42.1 | 1.16 |
| C) Na salt = sodium sulfate; N source = sodium glutamate | | | |
| 3.0 | 9.3 | 31.9 | 1.34 |
| 2.5 | 10.1 | 38.6 | 1.35 |
| 2.0 | 10.1 | 41.4 | 1.30 |
| 1.5 | 9.5 | 43.6 | 1.26 |

As seen in Table 8, omega-3 and total fatty acid production when using sodium sulfate is comparable to or better than when using sodium chloride as a sodium salt.

Example 14
Production of Schizochytrium in Low Salinity Culture Medium

This Example illustrates the fermentation of Schizochytrium in a low salinity culture medium while maintaining high biomass yields and high omega-3 and fatty acid production.

Schizochytrium ATCC No. 20888 was grown in medium, containing 3.33 g/l of peptone as a nitrogen source, 5.0 g/l of glucose as a carbon source, with varying sodium concentrations. The cells were fermented at 30° C. with an inoculum of about 40 mg/L dwt for a period of 48 hours. The sodium was supplied as sodium chloride. The results of this run are shown in Table 9.

TABLE 9

Production of Schizochytrium in Low Salinity Culture Medium

| Na conc. g/L | Cl conc. g/L | Biomass Yield g/L | Fatty acids % dwt | omega-3 % dwt | final glucose g/L |
|---|---|---|---|---|---|
| 4.88 | 7.12 | 1.76 ± 0.60 | 35.4 ± 1.0 | 10.2 ± 0.6 | 0.00 |
| 3.90 | 5.70 | 1.72 ± 0.67 | 37.0 ± 0.7 | 11.1 ± 0.3 | 0.15 |
| 2.93 | 4.27 | 1.70 ± 0.42 | 43.0 ± 0.2 | 12.1 ± 0.1 | 0.22 |
| 1.95 | 2.85 | 1.66 ± 0.57 | 29.8 ± 0.7 | 9.3 ± 0.1 | 1.55 |
| 0.98 | 1.42 | 0.40 ± 0.61 | 10.6 ± 2.4 | 4.0 ± 1.0 | 4.31 |

As can be seen from the results in Table 9, high biomass yields and production of omega-3 fatty acids and total fatty acids can be achieved at sodium concentrations of greater than about 1.0 g/l.

Example 15
Cultivation of Schizochytrium in Medium with Low Chloride Content

This Example illustrates the fermentation of microflora of the present invention at minimal chloride concentrations while achieving high biomass yields based on starting sugar concentration.

Schizochytrium ATCC No. 20888 was cultured in shake flasks at 200 rpm and 28° C. in 50 ml aliquots of the following medium. 1000 ml deionized water; 1.2 g MgSO$_4$.7H$_2$O; 0.067 g CaCO$_3$; 3.0 g glucose; 3.0 g monosodium glutamate; 0.2 g KH$_2$PO$_4$; 0.4 g yeast extract; 5.0 ml PII metals, 1.0 vitamin mix; and 0.1 g each of penicillin-G and streptomycin sulfate. The chloride concentration was varied by adding differing amounts of KCl to each treatment. The potassium concentration in all of the treatments was held constant by additions of potassium citrate. Sodium concentration was either 2.37 g/l or 4.0 g/l through addition of sodium sulfate. The results of these fermentations are shown below in Table 10.

TABLE 10

Fermentation of Schizochytrium at Minimal Chloride Concentrations

| Chloride conc. (mg/L) | Na 2.37 g/L Biomass Yield (mg/L) | Na 4.0 g/L Biomass Yield (mg/L) |
|---|---|---|
| 0.1 | 198 ± 21 | 158 ± 48 |
| 7.1 | 545 ± 120 | 394 ± 151 |
| 15.1 | 975 ± 21 | 758 ± 163 |
| 30.1 | 1140 ± 99 | 930 ± 64 |
| 59.1 | 1713 ± 18 | 1650 ± 14 |
| 119.1 | 1863 ± 53 | 1663 ± 46 |
| 238.1 | 1913 ± 11 | 1643 ± 39 |

As can be seen from the results shown in Table 10, high yields of biomass per sugar can be achieved at low chloride concentrations. For example, at a chloride concentration of greater than 59.1 mg/L, yields of greater than 50% are achieved.

Example 16
Variation of Sodium Sulfate Concentration at Low Chloride Concentrations This Example illustrates the effect of varying sodium sulfate concentration in a fermentation at low chloride concentration.

Schizochytrium ATC 20888 was cultured in shake flasks at 200 rpm and 28° C. in 50 ml aliquots of the following medium: 1000 ml deionized water; 1.2 g $MgSO_4 \cdot 7H_2O$; 0.125 g KCl; 0.067 g $CaCO_3$; 3.0 g glucose; 3.0 g monosodium glutamate; 0.2 g $KH_2PO_4$; 0.4 g yeast extract; 5.0 ml PII metals; 1.0 ml vitamin mix; and 0.1 g each of penicillin-G and streptomycin sulfate. The sodium sulfate concentration was varied in the treatments from 3.0 g/l to 30.2 g/l. The results of the fermentation runs are shown below in Table 11.

TABLE 11

Variation of Sodium Sulfate Concentration at Low Chloride Content

| Sodium Sulfate (g/l) | Biomass yield (g/l) |
|---|---|
| 3.0 | 0.78 |
| 6.0 | 1.13 |
| 9.1 | 1.72 |
| 12.1 | 1.88 |
| 15.1 | 1.89 |
| 22.7 | 1.91 |
| 30.2 | 1.63 |

The results shown in Table 11, illustrate that at a low chloride concentration of about 59 g/l, high biomass yields from glucose of greater than 50% can be obtained by selection of an appropriate sodium sulfate concentration.

What is claimed is:

1. A process for producing lipids comprising:
   (a) growing euryhaline microorganisms in a fermentation medium, wherein said euryhaline microorganisms are capable of producing about 1.08 grams per liter of the fermentation medium per day of long chain omega-3 fatty acids per 40 grams of sugar per liter of the fermentation medium at a sodium ion concentration in the fermentation medium of 60% seawater; and
   (b) extracting lipids from said euryhaline microorganisms.

2. The process of claim 1, wherein said euryhaline microorganisms have exponential growth rates of at least about 5 doublings per day at 25° C.

3. The process of claim 1, wherein said euryhaline microorganisms have exponential growth rates of at least about 7 doublings per day at 30° C.

4. The process of claim 1, wherein said euryhaline microorganisms are microorganisms of the order Thraustochytriales.

5. The process of claim 4, wherein said euryhaline microorganisms are selected from the group consisting of Thraustochytrium, Schizochytrium, and mixtures thereof.

6. The process of claim 5, wherein said euryhaline microorganisms are selected from the group consisting of ATCC 20888, ATCC 20889, ATCC 20890, ATCC 20891, ATCC 20892, and mixtures thereof.

7. The process of claim 1, wherein about 20% or less of the total fatty acids in said lipids are omega-6 fatty acids.

8. The process of claim 1, wherein at least about 49% of the total fatty acids of said lipids are omega-3 fatty acids.

9. The process of claim 1, wherein the ratio of docosahexaenoic acid (DHA) to eicosapentaenoic acid (EPA) in said lipids is about 7.07 or less.

10. The process of claim 1, wherein at least about 64.5% of omega-3 fatty acids in said lipids is DHA.

11. The process of claim 1, wherein at least about 86% of omega-3 fatty acids in said lipids is DHA.

12. The process of claim 1, wherein the ratio of EPA to DHA in said lipids is from about 1:1 to about 1:30.

13. The process of claim 1, wherein the ratio of DPA to DHA in said lipids is at least about 1:12.

14. The process of claim 1, wherein the total fatty acid composition in said lipids comprises about 5% or less of C20:4w6 fatty acid.

* * * * *

UNITED STATES PATENT AND TRADEMARK OFFICE
CERTIFICATE OF CORRECTION

PATENT NO. : 6,451,567 B1
DATED : September 17, 2002
INVENTOR(S) : Barclay

It is certified that error appears in the above-identified patent and that said Letters Patent is hereby corrected as shown below:

<u>Title Page,</u>
Item [63], please delete the exisiting "Related U.S. Application Data" and insert the following therefor:
-- This application is continuation-in-part of U.S. Patent Application Serial No. 08/968,628, filed November 12, 1997, now abandoned, which is a continuation of U.S. Patent Application Serial No. 08/461,137, filed June 5, 1995, which issued as U.S. Patent No. 5,688,500, which is a continuation of U.S. Patent Application Serial No. 08/292,490, filed August 18, 1994, which issued as U.S. Patent No. 5,518,918, which is a divisional of U.S. Patent Application Serial No. 07/962,522, filed October 16, 1992, which issued as U.S. Patent No. 5,340,742, which is a continuation-in-part of U.S. Patent Application Serial No. 07/911,760, filed July 10, 1992, which issued as U.S. Patent No. 5,340,594, which is a divisional of U.S. Patent Application Serial No. 07/580,778, filed September 11, 1990, which issued as U.S. Patent No. 5,130,242, which is a continution-in-part of U.S. Patent Application Serial No. 07/439,093, filed November 17, 1989, now abandoned, which is a continuation-in-part of U.S. Patent Application Serial No. 07/241,410, filed September 7, 1988, now abandoned. --

Signed and Sealed this

Twenty-fourth Day of December, 2002

JAMES E. ROGAN
*Director of the United States Patent and Trademark Office*

(12) EX PARTE REEXAMINATION CERTIFICATE (7357th)
United States Patent
Barclay

(10) Number: US 6,451,567 C1
(45) Certificate Issued: Feb. 9, 2010

(54) FERMENTATION PROCESS FOR PRODUCING LONG CHAIN OMEGA-3 FATTY ACIDS WITH EURYHALINE MICROORGANISMS

(75) Inventor: William R. Barclay, Boulder, CO (US)

(73) Assignee: Martek Biosciences Corporation, Columbia, MD (US)

Reexamination Request:
No. 90/009,073, Mar. 7, 2008

Reexamination Certificate for:
Patent No.: 6,451,567
Issued: Sep. 17, 2002
Appl. No.: 09/461,709
Filed: Dec. 14, 1999

Certificate of Correction issued Dec. 24, 2002.

Related U.S. Application Data

(63) Continuation-in-part of application No. 08/968,628, filed on Nov. 12, 1997, now abandoned, which is a continuation of application No. 08/461,137, filed on Jun. 5, 1995, now Pat. No. 5,688,500, which is a continuation of application No. 08/292,490, filed on Aug. 18, 1994, now Pat. No. 5,518,918, which is a division of application No. 07/962,522, filed on Oct. 16, 1992, now Pat. No. 5,340,742, which is a continuation-in-part of application No. 07/911,760, filed on Jul. 10, 1992, now Pat. No. 5,340,594, which is a division of application No. 07/580,778, filed on Sep. 11, 1990, now Pat. No. 5,130,242, which is a continuation-in-part of application No. 07/439,093, filed on Nov. 17, 1989, now abandoned, which is a continuation-in-part of application No. 07/241,410, filed on Sep. 7, 1988, now abandoned.

(51) Int. Cl.
A23L 1/314 (2006.01)
A23L 1/33 (2006.01)
A23L 1/325 (2006.01)
A23L 1/03 (2006.01)
A23L 1/315 (2006.01)
A23L 1/32 (2006.01)
A23L 1/36 (2006.01)
A23K 1/18 (2006.01)
A23K 1/00 (2006.01)
A23K 1/16 (2006.01)
A61K 31/185 (2006.01)
A61K 31/20 (2006.01)
A61K 31/202; C12P 7/64; C11B 1/00; C11B 1/10; A23L 1/212; A23L 1/20; A23L 1/30; A23L 1/31; C12N 1/14

(52) U.S. Cl. .......................... 435/134; 435/135; 435/171; 435/243; 435/257.1; 435/42; 435/946

(58) Field of Classification Search .......................... None
See application file for complete search history.

(56) References Cited

U.S. PATENT DOCUMENTS

| 2,879,162 A | 3/1959 | Baldini et al. |
|---|---|---|
| 2,890,989 A | 6/1959 | Anderson |
| 3,108,402 A | 10/1963 | Kathrein |
| 3,142,135 A | 7/1964 | Kathrein |
| 3,296,079 A | 1/1967 | Griffin et al. |
| 3,316,674 A | 5/1967 | Shirota |
| 3,444,647 A | 5/1969 | Takahashi |
| 3,647,482 A | 3/1972 | Yueh |
| 3,661,663 A | 5/1972 | Shannon |
| 3,667,969 A | 6/1972 | Kracauer |
| 3,761,588 A | 9/1973 | Tsuruoka et al. |
| 3,879,890 A | 4/1975 | Chen et al. |
| 3,882,635 A | 5/1975 | Yamanaka et al. |
| 3,908,026 A | 9/1975 | Neely et al. |
| 3,908,028 A | 9/1975 | Neely et al. |
| 3,924,017 A | 12/1975 | Lee et al. |
| 4,162,324 A | 7/1979 | Cassidy et al. |
| 4,229,544 A | 10/1980 | Haynes et al. |
| 4,232,122 A | 11/1980 | Zilliken |
| 4,304,794 A | 12/1981 | Dwivedi et al. |
| 4,341,038 A | 7/1982 | Bloch et al. |
| 4,367,178 A | 1/1983 | Heigel et al. |
| 4,405,649 A | 9/1983 | Jeffreys et al. |
| 4,474,773 A | 10/1984 | Shinitzky et al. |
| 4,554,390 A | 11/1985 | Curtain et al. |
| 4,588,600 A | 5/1986 | Suderman |
| 4,615,839 A | 10/1986 | Seto et al. |
| 4,634,533 A | 1/1987 | Somerville et al. |
| 4,670,285 A | 6/1987 | Clandinin et al. |
| 4,749,522 A | 6/1988 | Kamarei |
| 4,758,438 A | 7/1988 | Stroz et al. |

(Continued)

FOREIGN PATENT DOCUMENTS

| AU | 657259 | 3/1995 |
|---|---|---|
| AU | 687016 | 2/1998 |
| CA | 2072978 | 5/1991 |

(Continued)

OTHER PUBLICATIONS

Ellenbogen et al., Polyunsaturated Fatty Acids of Aquatic Fungi: Possible Phylogenetic Significance, Comp. Biochem. Physiol., 1969, pp. 805–811, vol. 29.

(Continued)

Primary Examiner—Evelyn Huang

(57) ABSTRACT

A process is provided for growing the microflora Thraustochytrium, Schizochytrium, and mixtures thereof, which includes the growing of the microflora in fermentation medium containing non-chlorine containing sodium salts, in particular sodium sulfate. In a preferred embodiment of the present invention, the process produces microflora having a cell aggregate size useful for the production of food products for use in aquaculture. Further disclosed is a food product which includes Thraustochytrium, Schizochytrium, and mixtures thereof, and a component selected from flaxseed, rapeseed, soybean and avocado meal. Such a food product includes a balance of long chain and short chain omega-3 highly unsaturated fatty acids. Further, a process for producing lipids includes a fermentation by growing euryhaline microorganisms which are capable of producing 1.08 grams per liter of the fermentation medium per day of long chain omega-3 fatty acids per 40 grams of sugar per liter of the fermentation medium at a sodium ion concentration of 60% seawater. The lipids are then extracted from the euryhaline microorganisms.

U.S. PATENT DOCUMENTS

| | | | |
|---|---|---|---|
| 4,764,392 | A | 8/1988 | Yasufuku et al. |
| 4,792,418 | A | 12/1988 | Rubin et al. |
| 4,822,500 | A | 4/1989 | Dobson, Jr. et al. |
| 4,871,551 | A | 10/1989 | Spencer |
| 4,874,629 | A | 10/1989 | Chang et al. |
| 4,911,944 | A | 3/1990 | Holub |
| 4,913,915 | A | 4/1990 | Tanaka |
| 4,918,104 | A | 4/1990 | Weiss et al. |
| 4,938,984 | A | 7/1990 | Traitler et al. |
| 4,957,748 | A | 9/1990 | Winowiski |
| 5,012,761 | A | 5/1991 | Oh |
| 5,023,091 | A | 6/1991 | Winowiski |
| 5,064,665 | A | 11/1991 | Klopfenstein et al. |
| 5,130,242 | A | 7/1992 | Barclay |
| 5,133,963 | A | 7/1992 | Ise |
| 5,234,699 | A | 8/1993 | Yeo |
| 5,272,085 | A | 12/1993 | Young et al. |
| 5,340,594 | A | 8/1994 | Barclay |
| 5,340,742 | A | 8/1994 | Barclay |
| 5,407,957 | A | 4/1995 | Kyle et al. |
| 5,415,879 | A | 5/1995 | Oh |
| 5,492,828 | A | 2/1996 | Premuzic et al. |
| 5,518,918 | A | 5/1996 | Barclay |
| 5,547,699 | A | 8/1996 | Iizuka et al. |
| 5,656,319 | A | 8/1997 | Barclay |
| 5,688,500 | A | 11/1997 | Barclay |
| 5,698,244 | A | 12/1997 | Barclay |
| 5,908,622 | A | 6/1999 | Barclay |
| 5,958,426 | A | 9/1999 | Moreau et al. |
| 5,985,348 | A | 11/1999 | Barclay |
| 6,054,147 | A | 4/2000 | Barclay |
| 6,103,225 | A | 8/2000 | Barclay |
| 6,177,108 | B1 | 1/2001 | Barclay |
| 6,410,281 | B1 | 6/2002 | Barclay |
| 6,451,567 | B1 | 9/2002 | Barclay |
| 6,566,123 | B1 | 5/2003 | Barclay |
| 6,607,900 | B2 | 8/2003 | Bailey et al. |
| 6,977,167 | B2 | 12/2005 | Barclay |
| 7,005,280 | B2 | 2/2006 | Barclay |
| 7,011,962 | B2 | 3/2006 | Barclay |
| 7,022,512 | B2 | 4/2006 | Barclay |
| 7,033,584 | B2 | 4/2006 | Barclay |
| 7,381,558 | B2 | 6/2008 | Barclay |
| 2006/0094089 | A1 | 5/2006 | Barclay |
| 2006/0160203 | A1 | 7/2006 | Barclay |
| 2006/0188969 | A1 | 8/2006 | Barclay |
| 2007/0082384 | A1 | 4/2007 | Barclay |
| 2007/0099280 | A1 | 5/2007 | Barclay |

FOREIGN PATENT DOCUMENTS

| | | |
|---|---|---|
| DE | 3213744 | 11/1982 |
| DE | 3603000 | 8/1987 |
| DE | 3920679 | 1/1991 |
| EP | 0231904 | 8/1987 |
| EP | 0404058 | 12/1990 |
| FR | 1557635 | 2/1969 |
| GB | 1466853 | 3/1977 |
| GB | 2098065 | 11/1982 |
| JP | 54-105081 | 8/1979 |
| JP | 58-196068 | 11/1983 |
| JP | 58-213613 | 12/1983 |
| JP | 60-087798 | 5/1985 |
| JP | 60-105471 | 6/1985 |
| JP | 61-170366 | 8/1986 |
| JP | 63-040711 | 2/1988 |
| JP | 63-237745 | 10/1988 |
| JP | 64-47721 | 2/1989 |
| JP | 1-215245 | 8/1989 |
| JP | 02-171127 | 7/1990 |
| JP | B H 03-071100 | 11/1991 |
| JP | 4-58847 | 2/1992 |
| JP | 4-152861 | 5/1992 |
| JP | 4-252145 | 9/1992 |
| JP | 4-271754 | 9/1992 |
| JP | A H 06-209718 | 8/1994 |
| JP | A H 06-237703 | 8/1994 |
| JP | A H 07-255387 | 10/1995 |
| JP | 08-502405 | 3/1996 |
| JP | H08-509355 | 10/1996 |
| JP | A H 08-322475 | 12/1996 |
| JP | A HEI09-084590 | 3/1997 |
| JP | A HEI09-110888 | 4/1997 |
| KR | 1994-7396 | 8/1994 |
| WO | WO 88/02989 | 5/1988 |
| WO | WO 88/10112 | 12/1988 |
| WO | WO 89/00606 | 1/1989 |
| WO | WO 91/07498 | 5/1991 |
| WO | WO 91/11918 | 8/1991 |
| WO | WO 91/14427 | 10/1991 |
| WO | WO 92/12711 | 8/1992 |
| WO | WO 94/08467 | 4/1994 |
| WO | WO 96/038051 | 12/1996 |

OTHER PUBLICATIONS

U.S. Appl. No. 07/241,410, filed Sep. 7, 1988, Barclay.

U.S. Appl. No. 07/439,093, filed Nov. 17, 1989, Barclay.

U.S. Appl. No. 08/968,628, filed Nov. 12, 1997, Barclay.

U.S. Appl. No. 11/875,578, filed Oct. 19, 2007, Barclay.

U.S. Appl. No. 11/927,297, filed Oct. 29, 2007, Barclay.

U.S. Appl. No. 11/928,371, filed Oct. 30, 2007, Barclay.

U.S. Appl. No. 11/928,419, filed Oct. 30, 2007, Barclay.

"CRC Handbook of Microalgal Mass Culture," Richmond, A. ed., CRC Press, Inc., Boca Raton, Florida, 1986, pp. 344–398.

"Eggs Developed That Don't Boost Cholesterol", Investors Daily, May 2, 1988.

"Enriched eggs", UEP–4, Aug. 22, 1998, pp. 1–2.

"Martek Receives Favorable Ruling in Europe for DHA Food Patent", News Release, May 12, 2005, 1 page.

"Saturated vs. Highly Unsaturated Lipids" date unknown, pp. 1–19.

Aaronson et al., "Microalgae as a Source of Chemicals and Natural Products", 1980, Elsevier, 14 pages.

Abbildungen aus Porter, D., 1990, S. 393, "Wachstums–und Entwicklungsstadien von Thraustochytriaceae", 1 page.

Abril and Barclay, "Production of Docosahexaenoic Acid–Enriched Poultry Eggs and Meat Using an Algae–Based Feed ingredient", Simopoulos AP (ed): The Return of ο3 Fatty Acids into the Food Supply. I. Land–Based Animal Food Products and Their Health Effects. World Rev Nutr Diet. Basel, Karger, 1998, vol. 83, pp. 77–88.

Ainsworth, "Introduction and Keys to Higher Taxa.," pp. 1–7, 1973, in The Fungi. An Advanced Treatise, vol. 4B, (G.C. Ainsworth et al. eds., Academic Press).

Ajuyah et al., "Dietary Antioxidants and Storage Affect Chemical Characteristics of w–3 Fatty Acid Enriched Broiler Chicken Meats," J. Food Sci., 1993, 58(1), 43–46.

Ajuyah et al., "Studies on canola seed in turkey grower diet: Effects on w–3 fatty acid composition of breast meat, breast skin and selected organs," Can. J. Anim. Sci., 1993, 73, 177–181.

Akimoto et al., "Metal Salts Requisite for the Production of Eicosapentaenoic Acid by a Marine Bacterium Isolated from Mackerel Intestines", pp. 504–508, 1991, JAOCS, vol. 68, Jul.

Akimoto et al., "Production of Eicosapentaenoic Acid by a Bacterium Isolated from Mackerel Intestines", JAOCS, vol. 67, No. 12 (Dec. 1990), pp. 911–915.

Ando et al., "Incorporation of n–3 Polyunsaturated Fatty Acids into Phospholipids of a Marine Bacterium vibrio sp. Cultivated with Sardine Oil", pp. 169–171, 1992, J. Ferm. Bioeng., vol. 73.

Bahnweg et al., "A New Approach to Taxonomy of the Thraustochytriales and Labyrinthulales", pp. 131–140, 1986, in The Biology of Marine Fungi, (S.T. Moss ed., Cambridge University Press).

Bahnweg et al., (1974) Amer. J. Bot., vol. 61(7), pp. 754–766.

Bahnweg, (1979) Veroff. Inst. Meeresforsch. Bremerh. vol. 17:245–268.

Bajpai et al., "Effects of Aging Mortierella Mycelium on Production of Archidonic and Eicosapentaenoic Acids", pp. 775–780, 1991, JAOCS, vol. 68, Oct.

Bajpai et al., "Eicosapentaenoic Acid (EPA) Formation; Comparative Studies with Mortierella Strains and Production by Mortierella elongata", pp. 1294–1298, 1991, Mycol. Res., vol. 95.

Bajpai et al., "Optimization of Production of Docosahexaenoic Acid (DHA) by Thraustochytrium aureum ATCC 34304", pp. 509–514, 1991, JAOCS, vol. 68, Jul.

Bajpai et al., "Production of Docosahexaenoic Acid by Thraustochytrium aureum", pp. 706–710, 1991, Appl. Microbiol. Biotechnol. vol. 35.

Barclay et al., "Development of a DHA Production Technology Using Schizochytrium: A Historical Perspective", accepted for publication in a book entitles "Single Cell Oil vol. 2" to be published by The American Oil Chemists Society, pp. 1–32.

Barclay et al., "Production of Docosahexaenoic Acid–Enriched Poultry Eggs and Meat Using an Algae–Based Feed ingredient", Simopoulos AP (ed): The Return of o3 Fatty Acids into the Food Supply. I. Land–Based Animal Food Products and Their Health Effects. World Rev Nutr Diet. Basel, Karger, 1998, vol. 83, pp. 61–76.

Barlow and Pike, "Humans, animals benefit from omega–3 polyunsaturated fatty acids," Feedstuffs, May 13, 1991, pp. 18–26.

Barr, J. S. (1981) "The phylogenetic and taxonomic implications of flagellar rootlet morphology among zoosporic fungi." BioSystems 14:359–370.

Bartnicki–Garcia, "The Cell Wall: A Crucial Structure in Fungal Evolution", pp. 389–403, 1988, in Evolutionary Biology of the Fungi, (A.D.M. Rayner et al. eds., Cambridge University Press).

Beach and Holz, Biochim Biophys Acta, 316:56–65 (1973).

Beach et al., 1974, pp. 16–24 "Biosynthesis of Oleic Acid and docosahexaenoic Acid by a Heterotrophic Marine Dinoflagellate Crypthecodinium cohnii," Biochimica et Biophysica Acta, vol. 369.

Behrens et al., "Eicosapentaenoic Acid from Microalgae", p. 623, col. 2, abstract No. 193025d, 1989, Chemical Abstracts, vol. 111, No. 21, Nov. 20.

Behrens et al., "Eicosapentaenoic Acid from Microalgae", pp. 253–259, 1989, Novel Microb. Prod. Med. Agric.

Bell and Henderson, pp. 115–118, 1990 "Molecular Species Composition of Phosphatidylcholine from Crypthecodinium cohnii in Relation to Growth Temperature", Lipids, vol. 25, No. 2.

Berrio et al. "Effect of Corn, Linseed and Menhaden Fish Oils on The Fatty Acid Pattern of Broiler Thigh Muscle", Abstract of the 8th Ann. Meeeting, Poultry Science, vol. 66, Supp. 1, 1987, p. 66.

Bingham et al. "Production of Specialty Lipids by Microalgae", Program and Abstracts of the 46th Annual Meeting of the Society for Industrial Microbiology, Aug. 13–18, 1989, p. 122.

Borowitzka and Borowitzka, 1988, Algal Biotechnology, Cambridge University Press, London, pp. 27–58.

Borowitzka and Borowitzka, 1988, Micro–Algal Biotechnology, Cambridge University Press, London, pp. 257–287.

Boswell et al., "SCO Production by Fermentative Microalgae", pp. 274–286, 1992, in Industrial Applications of Single Cell Oils (Kyle et al., eds.), American Oil Chemists' Society, Champaign, III.

Bremer "Physiological responses of some thraustochytrid fungi", Veroff. Inst. Meeresforsch. Bremerhaven Suppl. 5: 237–250 (1974).

Britton et al., "Shore Ecology of the Gulf of Mexico", University of Texas Press, Austin, 1989, p. 183.

Cavalier–Smith, "The Origin of Nuclei and of Eukaryotic Cells", pp. 463–468, 1975, Nature, vol. 256.

Cavalier–Smith, T. (1983) "A 6–kingdom classification and a unified phylogeny." In: Endocytobiology II: Intracellular Space as Oligogenetic System, H. E. A. Schenk and W. Schwemmler (eds.), De Gruyter (Berlin), pp. 1027–1034.

Cerda–Olmeda et al., "A Biography of Phycomyces", pp. 7–26, 1987, in Phycomyces, (Cerda–Olmeda et al. eds., CSH Laboratory).

Chamberlain, A. H. and Moss, S. T. (1988) "The thraustochytrids: a protist group with mixed affinities." BioSystems 21:341–349.

Chen et al. "C–Labeled fatty acids from microalgae", Developments in Industrial Microbiology, vol. 31 (Journal of Industrial Microbiology, Suppl. No. 5), 1990, pp. 257–264.

Cherian amd Sim, "Effect of Feeding Full Fat Flax and Canola Seeds to Laying Hens on the Fatty Acid Composition of Eggs, Embryos, and Newly Hatched Chicks," Poultry Sci., 1991, 70, 917–922.

Cohen and Ratlege, "Single Cell Oils", 2005, pp. 36–51.

Cohen et al., "Overproduction of gamma.–Linolenic and Eicosapentaenoic Acids by Algae", pp. 569–572, 1992, Plant Physiol., vol. 98.

Cole–Parmer Catalog, 1999–2000, pp. 124–130 and cover.

Combs, "Algae (Chlorella) as a Source of Nutrients for the Chicks," Science, 1952, 116, 453–454.

Couch et al., 1973, Lipids, 8(7):385–392.

Cruickshank, 1934, "Studies in Fat Metabolism in the Fowl" in Biochem. J., 28:965–977.

Dick, "Saprolegniales", pp. 113–144, 1973, in The Fungi. An Advanced Treatise, (G.C. Ainsworth et al. eds., Academic Press)).

Dictionary of Microbiology and Molecular Biology, P. Singleton and D. Sainsbury, 1978, pp. 406–408 and 332.

Edwards, Jr. and May, "Studies with Menhaden Oil in Practical–Type Broiler Rations," Poultry Sci., 1965, 44, 685–688.

Edwards, Jr. et al., "Carcass Composition Studies. 1. Influences of Age, Sex and Type of Dietary Fat Supplementation on Total Carcass and Fatty Acid Composition," Poultry Sci., 1972, 52, 934–948.

Emerson, "Current Trends of Experimental Research in the Aquatic Phycomycetes", pp. 169–200, 1950 Ann. Rev. Micro., vol. 4.

Erwin, "Comparative Biochemistry of Fatty Acids in Eukaryotic Microorganisms", pp. 41–143, 1973, in Lipids and Biomembranes of Eukaryotic Microorganisms, (J. Erwin ed., Academic Press).

Falbe, J. et al. (1990). Rompp Chemie Lexikon, pp. 286–287.

Findlay et al., "Biochemical Indicators of the Role of Fungi and Thraustochytrids in Mangrove Detrital Systems", pp. 91–103, 1986, in The Biology of Marine Fungi, (S.T. Moss ed., Cambridge University Press).

Fisher et al., 1957, J. Nutr., 63:119–129.

Fogg, G.E. Algal Cultures and Phytoplankton Ecology, 2nd ed., pp. 90–91, 1975, The University of Wisconsin Press.

Fry et al., "Fish Meal Studies. 2. Effects of Levels and Sources on "Fishy Flavor" Broiler Meat," Poultry Sci., 1965, 44, 1016–1019.

Fuller, et al., "Isolation and Pure Culture Study of Marine Phycomycetes", pp. 745–756, 1964, Mycologia, vol. 56.

Gaertner, 1968, "Eine methode des quantitativen Nachweises niederer, mit Pollen Koderbarer Pilze im Meerwasser und im Sediment" Veroff. Inst. Meeresforsch. Bremerh. Suppl. 3: 75–92.

Gaertner, A. (1967), Helgol. Wiss. Meeresunters. 15: 181–186.

Galvin et al., "Effect of dietary oil quality and .alpha.–tocopherol supplementation on the oxidative stability of broiler tissues," Proc. Nutrition Soc., 1994, 53(2), 13A.

Gandhi et al., "Production of the Polyunsaturated Fatty Acids Arachidonic Acid and Eicosapentaenoic Acid by the Fungus Pythium ultimum", pp. 1825–1830: 1991, J. Gen. Microbiol., vol. 137.

Gellerman et al., "Methyl–Directed Desaturation of Arachidonic to Eicosapentaenoic Acid in the Fungus, Saprolegnia parasitica", pp. 23–30, 1979, Biochim. Biophys. Acta, vol. 573.

Goldstein (1973) Am. Rev. Micro., 27:13–26.

Goldstein et al., "Biology of a Problematic Marine Fungus, Dermocystidium sp. I. Development and Cytology", pp. 1–11, 1966, Archiv for Mikrobiologie, vol. 53.1.

Goldstein et al., "Biology of a Problematic Marine Fungus, Dermocystidium sp. II. Nutrition and Respiration", pp. 468–472, 1969, Mycologia, vol. 61.

Goldstein, "Development and Nutrition of New Species of Thraustochystrium", pp. 271–279, 1963, Am. J. bot., vol. 50.

Goldstein, S. (1963 b), Arch. Mikrobiol. 45: 101–110.

Goldstein, S. (1963 c) Mycologia 55(6): 799–805.

Goldstein, S. and Belsky, M. (1964), Am. J. Bot. 51(1):72–75.

Granger et al., "Kinetics of Growth and Fatty Acid Production of Rhodotorula glutinis" pp. 13–17, 1992, Appl. Microbiol. Biotechnol, vol. 37.

Hansen et al., "Effects of Culture Conditions on Accumulation of Arachidonic and Eicosapentaenoic Acids in Cultured Cells of Rhytidiadelphus squarrosus and Eurhynchium Striatum", pp. 1837–1841, 1991, Phytochemistry, vol. 30.

Hargis, "Designing Eggs for the Health Conscious Consumer," Egg Industry, Nov./Dec. 1992, 24–30.

Harrington et al. (1970) J. Protozool, vol. 17(2), pp. 213–219.

Harrington et al., 1968, Biochim. Biophys. Acta, 164:137–39.

Harwood, "Plant Acyl Lipids: Structure, Distribution, and Analysis" in The Biochemistry of Plants, pp. 2–48, 1980, vol. 4, Academic Press, Inc.

Haskins et al., Steroids and the Stimulation of Sexual Reproduction of a Species of Pythium, Canadian J. Microbiology, 10:187–195 (1964).

Henderson et al., "Lipid Composition and Biosynthesis in the Marine Dinoflagellate Crypthecodinium Cohnii", pp. 1679–1683, 1988, Phytochemistry, vol. 27. No. 6.

Holliday, Salinity. In:Kinne (1971), Marine Ecology, A Comprehensive . . . vol. 1, Part 2: pp. 997, 1023–1025.

Honda, D. et al. (1998) Mycol. Res. 102(4): 439–448.

Hori and Osawa (1986) "Evolutionary change in 5SrRNA secondary structure and a phylogenetic tree of 352 5S rRNA species", Biosystems 19: p. 163–172.

Hori et al., "The Nucleotide Sequence of 5S rRNA from a Cellulai Slime Mold Dictyostelium discoideum", pp. 5535–5539, 1980, Nucl. Acids Res., vol. 8.

Horne, R.A., Marine Chemistry, 1969, Wiley & Sons, pp. 150–163 and 486–487.

Hulan and Proudfoot, "Replacement of Soybean Meal in Chicken Broiler Diets by Rapeseed Meal and Fish Meal Complementary Sources of Dietary Protein," Can. J., Anim. Sci., 1981, 61, 999–1004.

Hulan et al., "Omega–3 Fatty Acids Levels and General Performance of Commercial Broilers Fed Practical Levels of Redfish Meal," Poultry Sci., 1989, 68, 153–162.

Hulan et al., "The Broiler Chicken as an Alternative to Fish and Shellfish as a Dietary Source of Eicosapentaenoic Acid," Poultry Sci. vol. 65 Suppl., p. 60, Abstract, 75th Ann. Meeting.

Hulan et al., "The Effects of Different Dietary Fat Sources on General Performance and Carcass Fatty Acid Composition of Broiler Chickens," Poultry Sci., 1984, 63, 324–332.

Hulan et al., "The Effects of Feeding Fish Meal on the General Performance, Omega–3 Fatty Acid Composition and sensory Characteristics of Broiler Chickens", Abstract of the 8th Ann. Meeeting, Poultry Science, vol. 66, Supp. 1, 1987, p. 1.17.

Hunter, "Fish Oil and Other Omega–3 Sources", pp. 1592–1596, J. Am. Oil Chem. Soc., vol. 64.

International Dictionary of Medicine and Biology (1986) pp. 1042 and 1267.

Jones et al., (1976) Elek Science, pp. 261–272.

Jong et al., "American Type Culture Collection Catalogue of Fungi/Yeast", pp. 350 and 378, American Type Culture Collection, 17th Edition, 1987.

Karlenskind (ed), Oils and Fats Manual, vol. 1, 1996, p. 67–68 and 81.

Kates, "Techniques of Lipidology: Isolation, Analysis and Identification of Lipids", pp. 186–278, 1986, Laboratory Techniques in Biochemistry and Molecular Biolgy, vol. 3.

Kazama, F (1980) The zoospore of Schizoshytrium aggregatum. Can J. Bot. 58:2434–2446.

Kendrick et al., "Lipids of Selected Molds Growth for Production on n–3 and n–6 Polyunsaturated Fatty Acids", pp. 15–20, 1992, Lipids, vol. 27.

Kendrick et al., "Microbial Polyunsaturated Fatty Acids of Potential Commercial Interest", pp. 59–65, 1992, SIM Industrial Microbiology News, vol. 42.

Kinne, (1977), Marine Ecology, A Comprehensive . . . vol. III, Part 2: pp. 584–591.

Kinne, In:Temperature (1971), Marine Ecology, A Comprehensive . . . vol. 1, Part 2: pp. 407, 430, 431, 432, 433.

Kinne, (1970), Marine Ecology, A Comprehensive . . . vol. I, Part 1: pp. 820–823, 876–885, 940–941, 952–953.

Klausner "Algaculture: Food For Thought", BioTechnology, vol. 4, Nov. 1986, pp. 947–948, 952–953.

Kohlmeyer et al., Marine Mycology (1979), pp. 2–3.

Krogdahl, "Digestion and Abosorption of Lipids in Poultry," J. Nutrition, 1985, 115, 675–685.

Kyle et al. (1989) "Microalgae as a Source of EPA," presented at the International Composium for New Aspects of Dietary Lipids and Uses at the University of Phos., Sweden, pp. 161–169.

Kyle et al., "Bioproduction of Docosahexaenoic Acid (DHA) by Microalgae", pp. 287–300, 1992, in Industrial Applications of Single Cell Oils (Kyle et al., eds.), American Oil Chemists' Society, Champaign, IL.

Kyle et al., "Microalgae as a Source of EPA–Containing Oils", pp. 117–121, 1988, Proc.–World Conf. Biotechnol. Fats Oils Ind.

Kyle, "Microalgae as a Source of EPA–Containing Oils," p. 495, col. 2, abstract No. 22136, 1988, Chemical Abstracts, vol. 111, No. 3, Jul. 17, 1989.

Lee et al., (1971) Phytochemistry, vol. 10, pp. 593–602.

Lepage et al., "Improved Recovery of Fatty Acid Through Direct Transesterification Without Prior Extraction or Purification", pp. 1391–1396, 1984, J. Lipid Res., vol. 25.

Leskanich and Noble, "Manipulation of the n–3 polyunsaturated fatty acid composition of avian eggs and meat," World's Poultry Science Journal, 1997, 53, 155–183.

Leveille et al., "Protein Value and the Amino Acid Deficiencies of Various Algae for Growth of Rats and Chicks," J. Nutrition, 1962, 76, 423–428.

Lewis et al., "Production of Polyunsaturated Fatty Acids by Australian Thraustochytrids: Aquaculture Applications" from "Hatchery feeds for aquaculture" Proceedings of a workshop held in Caims Mar. 9–10, 2000.

Lipstein et al., "The Nutritional and Economic Value of Algae for Poultry" in Algae Biomass, G. Shelef and C.J. Soeder, eds., Elsevier/North–Holland Biomedical Press, 1980, pp. 667–685.

Lipstein et al., "The Nutritional Value of Algae for Poultry. Dried Chlorella in Layer Diets," Br. Poultry Sci., 1980, 21, 23–27.

Lipstein et al., 1980, Br. Poultry Sci., 21:9–21.

Loosanoff, V. (1950), On behavior of oysters transferred from low to high salinities. Anatomical Record 108:579.

Lovell "Incresing Omega–3 Fatty Acids In Famed Catfish", Aquaculture Magazine, Sep./Oct. 1988 pp. 54–55.

Mackereth et al., Water Analyses, 1978, pp. 47–49.

Mannella et al., "Interrelatedness of 5S RNA Sequences Investigated by Correspondence Analysis", pp. 228–235, 1987, J. Mol. Evol., vol. 24.

Marguilis, L. and Sagan, D. (1985) "Order amidst animalcules: the Proctoctista kingdom and its undulipodiated cells." BioSystems 18:141–147.

Marion and Woodroof, "The Fatty Acid Composition of Breast, Thigh, and Skin Tissues of Chicken Broilers as Influenced by Dietary Fats," Poultry Sci., 1963, 42, 1202–1207.

Markson LabSales, 1998 Master Catalog, pp. 65–69 and cover.

McLachlan, "Some Considerations of the Growth of Marine Algae in Artificial Media", Canadian Journal of Microbiology, vol. 10, 1964, pp. 769–782.

McLeod, "Nutritional Factors Influencing Carcase Fat in Broilers—A Review," Worlds Poultry Science Journal, 1981, 37, 194–200.

McLusky D. (1989) The Estuarine Ecosystem. 2nd Ed. Chapman and Hall, New York. pp. 104–105.

Metting "Microalgae Applications in Agriculture", Program and Abstracts of the 46th Annual Meeting of the Society for Industrial Microbiology, Aug. 13–18, 1989, p. 122.

Miller and Robisch, "Comparative Effect of Herring, Menhaden, and Safflower Oils on Broiler Tissues Fatty Acid Composition and Flavor," Poultry Sci., 1969, 48, 2146–2157.

Miller et al., "Dietary Effect of Menhaden–Oil Ethyl Esters on the Fatty Acid Pattern of Broiler Muscle Lipids," Poultry Sci., 1967, 46, 438–444.

Miller et al., "Effect of Dietary Fat on Tissue Fat and Plasma Cholesterol Level in Broilers," Poultry Sci., 1962, 41, 970–974.

Miller et al., "Effect of Feeding and Withdrawal of Menhaden Oil on the w3 and w6 Fatty Acid Content of Broiler Tissues," J. Food Sci., 1969, 34, 136–141.

Miller et al., "Effect of Refined Menhaden Oils on the Flavor and Fatty Acid Composition of Broiler Flesh," J. Food Sci., 1967, 32, 342–345.

Miller, "Isolation and Pure Culture of Aquatic Phycomycetes by Membrane Filtration", pp. 524–527, 1967, Mycologia, vol. 59.

Mokady et al., "Nutritional Evaluation of the Protein of Several Algae Species for Broilers," Arch. Hydrobiol. Beih. Ergebn. Limmol., 1978, 11, 89–97.

Mokady et al., "Protein Nutritive Value of Several Microalgae Species for Young Chickens and Rats," Algae Biomass, Shelef and Soeder, eds., Elsevier/North–Holland Biomedical Press, 1980, pp. 655–660.

Moore–Landecker, "Growth of Fungi in Culture", Fundamentals of the Fungi, 1982, pp. 280–307.

Moreton (ed)., "Physiology of Lipid Accumulated Yeasts", in single Cell Oil, pp. 1–31, 1988, John Wiley & sons, Inc., New York.

Moss, "Biology and Phylogeny of the Labrinthulales and Thraustochytriales", pp. 105–129, 1986, in The Biology of Marine Fungi, (S.T. Moss ed., Cambridge University Press).

Motion For Summary Judgment Letter in Civil Action No. 03–896–GMS dated Mar. 14, 2006, pp. 1–3.

Murty et al., 1961, J. Nutrition, 75:287–294.

n–3 News Unsaturated Fatty Acids and Health, Mar. 1988, vol. III, No. 1, pp. 1–4.

Navarro et al., 1972, J. Sci. Fd. Agric., 23:1287–1292.

Neudoerffer et al., "Effects of dietary fish oil on the composition and stability of turkey depot fat," Br. J. Nutr., 1966, 20, 581–594.

Nir, "Performance of Broilers Fed Diets Supplemented with 1.5% Soybean or Redfish Oil," Poultry Sci. Suppl., Abstract of Papers, 1990, 69(1), p. 99.

Nwokolo and Sim, "w–3 Fatty Acid Enrichment of Broiler and Layer Tissues, and Egg Yolk by Feeding Flax and Canola Seed Diets," Poultry Sci. vol. 68: Suppl.; 1990, p. 106, Abstract, 78th Ann. Poultry Sci. Assn. Mtg.

Opstvedt et al., "Influence of Residual Lipids on the Nutritive Value of Fish Meal," Acta Agri. Scand., 1970, 20, 185–193.

Opstvedt, "Influence of Residual Lipids on Nutritive Value of Fish Meal," Acta Agric. Scand., 1973, 23, pp. 217–224.

Opstvedt, "Influences of Residual Lipids on Nutritive Value of Fish Meal," Acta Agric. Scand., 1973, 23, 200–208.

Orcutt and Peterson, Sterol, Fatty Acid and Elemental Composition of Diatoms Grown in Chemically Defined Media, Comp. Biochem. Physiol., 50B:579–83(1975).

Perkins, "Phylogenetic Considerations of the Problematic Thraustochytriaceous–Labrinthulid–Dermocystidium Complex Based on Observations of Fine Structure", pp. 45–63, 1974, Veroff. Inst. Meeresforsch. Bremerh. Suppl., vol. 5.

Phetteplace and Watkins, "Dietary n–3 Fatty Acids Lowered Plasma Triacylglycerols in Male Broilers," Poultry Sci., vol. 68: Suppl. 1: 1990, p. 114, Abstract, 78th Ann. Poultry Sci. Assn. Mtg.

Phetteplace et al., "Effects of Dietary n–6 and n–3 Fatty Acids on Lipid Metabolism in Two Genetic Lines of Broilers," Poultry Sci., Vol. 68: Suppl. 1: 1990, p. 114, Abstract, 78th Ann. Poultry Sci. Assn. Mtg.

Pigott, "The Need to Improve Omega–3 Content of Cultured Fish", pp. 63–68, 1989, World Aquaculture, vol. 20.

Pirt "Aeration and Agitation Methods", in Principles of Microbe and Cell Cultivation, pp. 94–106, first published 1975, Blackwell Scientific Publications.

Pohl et al., "Fatty Acids and Lipids of Marine Algae and the Control of Their Biosynthesis by Environmental Factors", pp. 473–523, 1979, Marine Algae in Pharmaceutical Science, (Hoppe et al. eds.).

Porter (1974) "Phylogeneic considerations of the Thraustochytriaceae and Labrinthulaceae", Veroff. Inst. Meeresforsch. Bremerh. Suppl. 5:19–44.

Porter, (1989), "Studies on the Physiology of Thraustochytriales . . . ", Handbook of Protoctista, Jones and Bartlett Publishers, Chapter 22, pp. 388–398.

Provasoli et al. (1962) Archiv fur Mikrobiologie, vol. 42: pp. 196–203.

Provasoli et al., (date unknown), "Growing Marine Seaweeds," based on two communications: L. Provasoli, "Bacteria–free Culture and Nutrition of Some Seaweeds" and L. Provosoli et al., "Culture Media for Seaweeds", pp. 9–17.

Radwan, "Sources of $C_{20}$—Polyunsaturated Fatty Acids for Biotechnical Use", pp. 421–430, 1991, Appl. Microbiol. Biotechnol., vol. 35.

Raghukumar and Schaumann, "An epifuorescence microscopy method for direct detection and enumeration of the fungilike marine protists, the thraustochytrids", Limnol. Oceannogr., 38(1), 1993, 182–187.

Raghukumar et al., "Abundance of Thraustochytrid Fungi in the Arabian Sea", pp. 351–358, 1990, in Estuarine—Coastal and Shelf Science, vol. 31.

Raghu–Kumar, S. (1988 a), Trans. Br. Mycol. Soc. 90(4): 627–631.

Raghu–Kumar, S. (1988 b), Trans. Br. Mycol. Soc. 90(2): 273–278.

Ratledge, Biotechnology of Oils and Fats, 1989, pp. 566–583.

Reid, G.K., Ecology of Inland Waters and Estuaries, 1961, Reinhold Publishing Corporation, pp. 294–295.

Reiser, 1951, J. Nutrition, 44:159–175..

Rompps Chemielexikon 9, Auflage 1991, Seiten 2669 and 2670, Stichwort: Meerwasser zwei zustzliche Eingabenkopien eischliesslich Analagen.

Rouser et al., pp. 425–427, 1963, "Lipid Composition of Beef Brain, Beef Liver, and the Sea Anemone: Two Approaches to Quantitiative of Complex Lipid Mixtures", The Journal of the American Oil Chemists' Society, vol. 40.

Ryther, "Cultivation of Macroscopic Marine Algae", pp. 79–88, 1983, Solar Energy Research Institute Aquatic Species Program Review. Proc of the Mar. 1983 Principal Investigators Meeting, SERI/CP/–231 1946.

Schlegel, General Microbiology, 7th edition, cover page and p. 196.

Schlenk, "Urea Inclusion Compounds of Fatty Acids", pp. 243–267, 1954, Prog. Chem. Fats and Other Lipids, vol. 2.

Schneider, "Cultivation of Micro–organisms. Section 3.2: Fungi", pp. 337–345, 1976, in Marine Ecology, vol. 3, Part 1. Cultivation, (O. Kinne ed., Wiley and Sons).

Schneider, "Zur Taxonomie, Verbreitung und Okologie einiger mariner Phycomyceten", Aus dem Institut fur Meereskunde an der Universistat Kiel, 1969, pp. 316–327.

Schneider, J. (1967), Kieler Meeresforsch. 23: 16–20.

Sell et al., "Fatty Acid Composition of Egg Yolk and Adipose Tissue as influenced by Dietary Fat and Strain of Hen," 1968, 47, 1296–1302.

Seto et al., (1984) JAOCS, 61(5):892–894.

Shimizu et al. "Fungal Mycelia as a Novel Source of Eicosapentaenoic Acid", Biochemical and Biophysical Research Communications, vol. 150, No. 1, Jan. 15, 1988, pp. 335–341.

Shimizu et al. "Production of Eicosapentaenoic Acid by Mortierella Fungi", JAOCS, vol. 65, No. 9, (Sep. 13, 1988), 1455–1459.

Shimizu et al., "Microbial Conversion of an Oil Containing alpha–Linolenic Acid to an Oil containing Eicosapentaenoic Acid", JAOCS, vol. 66, No. 3, Mar. 1989, pp. 342–347.

Simopoulos et al. (eds.), Health Effects of Polyunsaturated Fatty Acids in Seafoods, Chaps. 2–5, 7, 17, 1986, Academic Press.

Siversand et al. "Improved High–performance liquid chromatographic method for the separation and quatification of lipid classes: application to fish lipids", Journal of Chromatography B. 703 (1997) pp. 7–14.

Sonnenbom and Kunau, pp. 523–534, 1982, Purification and Properties of the Fatty Acid Synthetase Complex from the Marine Dinoflagellate, Crypthecodinium cohnil, Biochimica et Biophysica Acta, vol. 712.

Sorokin, "Dry Weight, Packed Cell Volume and Optical Density", pp. 321–343, 1973 in Handbook of Phycological Methods: Culture Methods and Growth Measurements, (J.R. Stein ed., Cambridge University Press).

Sparrow (1973) "Mastigomycotina (zooporic fungi)"In: The Fungi, An Advanced Treatise, Ainsworth, Sparrow and Sussman (eds.), Academic Press, N.Y., pp. 61–73.

Sparrow, Aquatic Phycomycetes, pp. 36–39, 1960, University of Michigan Press.

Sparrow, F.K. (1936), Bio. Bull. 70: 236, 237, 259–263.

Stanbury et al., "Principles of Fermentation Technology" (1984), pp. 121–123, 236–237, 242–243.

STN Database, AN 88:13222 Biobusiness for Milchwissenschaft, 1988 vol. 43, No. 3, pp. 153, 155–158 Author: Hagemeister et al.

STN Database, AN 89:532569 Caplus for WO 88–US2483 published Jul. 20, 1988, Author T. Long.

Ter Mulen, U. et al., "Metabolic Studies on the Antioxidant Ethooxyquin", Journal of Animal Physiology, Animal Feed Information, No. 3 (1980), pp. 164–170, vol. 43.

Todorov, D., "Possibilities for Increasing the Biological Value of Alimentary Protein", Khigzdravfodaz, 1978, 21(3), p. 291–297.

Tornabene, 1974, Lipids, 9(4):279–284.

Tuttle et al., (1975) Phycologia, vol. 14, pp. 1–8.

Ukeles (1976) Marine Ecology, A Comprehensive . . . vol. III, Part 1, pp. 447–451.

Ulken, A. et al. On the role of Phycomycates in the food web of different mangrove swamps with brackish waters and waters of high salenity; European Marine Biology Symposium, 1981, Abstract from Sep. 29, 1990, Abstract AN 81:19970.

van der Werth, A. "Olgenwinnung durch Extraktion" (including translation) in "Chemie and Technologie der Fette und Fettprodukte", Julius Springer, Wien, 1936, pp. 680–683.

Van Winkle (1968). The effects of season, temperature, and salinity on the oxygen consumption of bivalve gill tissue. Comp. Biochem. Physiol. 26: 69–80.

Van Winkle (1970). Effect of environmental factors on byssal thread formation. Marine Biology 7: 143–148.

Vishniac, (1955) "Division of Mycology," pp. 352–360.

Vishniac, (1960) Limnol. Oceanogr 5:362–365.

Voet et al., Biochemistry, 2nd Edition, 1995, John Wiley & Sons, Inc., p. 279.

Vogel, H.U.v. (1974). Chemiker–Kalender, Springer Verlag, Berlin, p. 1605.

VWR Catalog, 2000/2001, 6 pages.

Wakelyn "Regulatory Considerations for Extraction Solvents for Oilseeds and other nonpetroleum Oils" in Edible Oil Processing, Sheffield Academic Press 2000, pp. 49–51.

Waldroup et al., "Fish Meal Studies. 1. Effects of Levels and Sources on Broiler Growth Rate and Feed Efficiency," Poultry Sci., 1965, 44, 1012–1016.

Walz et al., "Studies on Some Nutritive Effects of the Green Algae Scenedesmus acutus with Pigs and Broilers," Algae Biomass, Shelef and Soeder, eds., Elsevier/North–Holland Biomedical Press, 1980, pp. 733–744.

Wassef, "Fungal Lipids", pp. 159–232, 1977, Adv. Lipid Res., vol. 15.

Weete, "Fatty Acids", Chapter 3, pp. 49–95, 1980, in Lipid Biochemistry of Fungi and Other Organisms, (Plenum Press).

Wessinger "Production of Long–Chain–Polyunsaturated Fatty Acids by Selected Species", Program and Abstracts of the 46th Annual Meeting of the Society for Industrial Microbiology, Aug. 13–18, 1989, p. 74.

Wetzel, Limnology, 1975, pp. 142–165.

Wheeler et al., "Fatty Acid Distribution in Egg Yolk as Influenced by Type and Level of Dietary Fat," J. Nutrition, 1959, 69, 253–257.

Yamada et al., "Production of Arachidonic Acid and Eicosapentaenoic Acid by Microorganisms", p. 1254, 1987, J. Am. Oil Chem. Soc., vol. 64.

Yamada et al., "Production of Dihomo–gamma.–Linolenic Acid, Arachidonic Acid and Eicosapentaenoic Acid by Filamentous Fungi", pp. 118–138, 1992, in Industrial Application of Single Cell Oils (Kyle et al., eds.), American Oil Chemists' Society, Champaign, IL.

Yannai et al., "The Safety of Several Algae Grown on Wastewater as a Feedstuff for Broilers," Arch. Hydrobiol. Beih. Ergebn. Limmol., 1978, 11, 139–149.

Yau et al., "Enrichment of Selected Fatty Acids in Broiler Tissues," Poultry Sci., vol. 68: Suppl. 1: 1990, p. 162, Abstract, 78th Ann. Poultry Sci. Assn. Mtg.

Yazawa et al., "Production of Eicosapentaenoic Acid by Marine Bacteria", J. Biochem. 103, 5–7 (1988).

Yazawa et al., "Production of Eicosapentaenoic Acid from Marine Bacteria", pp. 29–51, 1992, in Industrial Applications of Single Cell Oils (Kyle et al., eds.), American Oil Chemists' Society, Champaign, Ill.

Yongmanitchal et al., "Growth of and Omega–3 Fatty Acid Production by Phaeodactylum", Applied and Environmental Microbiology, Feb. 1991, pp. 419–425.

Yongmanitchal et al., "Omega–3 Fatty Acids: Alternative Sources of Production", pp. 117–125, 1989, Proc. Biochem.

Yongmanitchal et al., "Screening of Algae for Potential Alternative Sources of Eicosapentaenoic Acid", pp. 2963–2967, 1991, Phytochemistry, vol. 30.

Zoosporic Fungi in Teaching & Research (1987), Fuller et al. (eds.), p. 7, 110–116, 128–129, 294–298.

Written Opinion for International (PCT) Patent Application No. PCT/US98/16892, mailed May 27, 1999.

International Preliminary Examination Report for International (PCT) Patent Application No. PCT/US90/6375, mailed Dec. 5, 1995.

International Preliminary Examination Report for International (PCT) Patent Application No. PCT/US93/09679, mailed Mar. 20, 1995.

International Preliminary Examination Report for International (PCT) Patent Application No. PCT/US98/16892, mailed Dec. 9, 1999.

International Search Report for International (PCT) Patent Application No. PCT/US90/6375, mailed Feb. 26, 1991.

International Search Report for International (PCT) Patent Application No. PCT/US93/09679, mailed Jan. 19, 1994.

International Search Report for International (PCT) Patent Application No. PCT/US98/16892, mailed Nov. 17, 1998.

Barr, J. S. (1983) "The zoosporic grouping of plant pathogens." In: Zoosporic Plant Pathogens: a modern perspective, S. T. Buczacki (ed.), Academic Press, pp. 43–83.

Cohen et al. (1988) "Effect of environmental conditions on fatty acid composition of the red alga Porphyridium cruentum: correlation to growth rate", J. Phycol. 24: 328–332.

Dansky, "The Growth Promoting Properties of Menhaden Fish Oil as Influenced by Various Fats," Poultry Sci., 1962, 41, 1352–1354.

Emerson, "Current Trends of Experimental Research in the Aquatic Phycomycetes", pp. 169–200, 1950, Ann. Rev. Micro., vol. 4.

Harwood, "Plant Acyl Lipids: Structure, Distribution, and Analysis" in The Biochemistry of Plants, pp. 2–48, 1980, vol. 4, Academic Press, Inc.

Holliday, FGT (1971) 4. Salinity, 4.3 Animals. 4.32 Fishes. pp. 997–1033, in O. Kinne (ed), Marine Ecology, vol. 1 Environmental Factors, Part 2, John Wily and Sons, London.

Leedale, G. (1974) "How many are the kingdoms of organisms." Taxon 23:261–270.

Perkins, F. O. (1976) "Fine structure of lower marine and estuarine fungi." In: Recent Advances in marine Mycology, E. B. Gareth Jones (ed.), Elek Science, pp. 279–312.

Poyton, R. (1970) "The characterization of Hyallochlorella marina gen. et sp. nov. a new colorless counterpart of Chlorella." J. Gen. Microbiol. 62:171–188.

Rouser et al., pp. 425–454, 1963, "Lipid Composition of Beef Brain, Beef Liver, and the Sea Anemone: Two Approaches to Quantititative Fractionation of Complex Lipid Mixtures", The Journal of the American Oil Chemists' Society, vol. 40.

Sargent, J. et al. (1989), "The lipids," in Fish Nutrition, Second Edition, J. Halver (ed)., Academic Press, pp. 153–218.

Simopoulos et al., (1986) Purslane: a terrestial source of w–3 fatty acid, N. Engl. J. Med. 315:833.

Ukeles (1976) Marine Ecology, A Comprehensive . . . vol. III, Part 1, pp. 367–466.

Kinne (1971), Marine Ecology, A Comprehensive . . . vol. 1, Part 2: pp. 821–995.

Kinne, (1970), Marine Ecology, A Comprehensive . . . vol. 1, Part 1: pp. 405–514.

Kyle, "Microalgae as a Source of EPA–Containing Oils", p. 1251, 1987, J. Am. Oil Chem. Soc., vol. 64.

Gaertner, A. (1970), Veroff. Inst. Meeresforsch. Bremerh. 12: 321–327. (Translated abstract).

Gaertner, A. (1981), Veroff. Inst. Meeresforsch. Bremerh. 19: 61–69. (Translated abstract).

Jennings "Some Aspects of the Physiology and Biochemistry of Marine Fungi", Biol. Rev. (1983), 58, pp. 423–459.

Federal Circuit Decision in U.S. Court of Appeals for the Federal Circuit Case No. 2008–1459,–1476, decided Sep. 3, 2009, 36 pages.

Defendant–Appellant Lonza, Ltd.'s Combined Petition for Rehearing and Rehearing En Banc of the Federal Circuit Decision of Sep. 3, 2009 in U.S. Court of Appeals for the Federal Circuit Case No. 2008–1459,–1476, executed Oct. 5, 2009, 58 pages.

Documents from File History for European Opposition of European Patent No. 0512997, dated between Jun. 15, 2009 to Jun. 25, 2009.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–14 are cancelled.

* * * * *